(12) United States Patent
Baba-Ahmed et al.

(10) Patent No.: US 10,494,320 B2
(45) Date of Patent: Dec. 3, 2019

(54) METHOD FOR PRODUCING AND PURIFYING 2,3,3,3-TETRAFLUORO-1-PROPENE

(71) Applicant: Arkema France, Colombes (FR)

(72) Inventors: Abdelatif Baba-Ahmed, Saint-fons (FR); Bertrand Collier, Saint-genis-laval (FR); Dominique Deur-Bert, Charly (FR); Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 16/063,304

(22) PCT Filed: Dec. 14, 2016

(86) PCT No.: PCT/EP2016/080948
§ 371 (c)(1),
(2) Date: Jun. 18, 2018

(87) PCT Pub. No.: WO2017/108522
PCT Pub. Date: Jun. 29, 2017

(65) Prior Publication Data
US 2018/0370881 A1    Dec. 27, 2018

(30) Foreign Application Priority Data
Dec. 23, 2015 (FR) ..................... 15 63167

(51) Int. Cl.
*C07C 17/386* (2006.01)
*C07C 17/25* (2006.01)
(Continued)

(52) U.S. Cl.
CPC ............ *C07C 17/386* (2013.01); *C07C 17/25* (2013.01); *C07C 19/03* (2013.01); *C07C 21/18* (2013.01);
(Continued)

(58) Field of Classification Search
CPC .................................................... C07C 17/386
See application file for complete search history.

(56) References Cited

U.S. PATENT DOCUMENTS

| 2015/0005537 A1* | 1/2015 | Furuta .................. C07C 17/269 570/159 |
| 2015/0203422 A1* | 7/2015 | Deur-Bert ............ C07C 17/206 570/156 |
| 2015/0291490 A1 | 10/2015 | Furuta et al. |

FOREIGN PATENT DOCUMENTS

EP    2826766 A1    1/2015

OTHER PUBLICATIONS

EPO, International Search Report in International Patent Application No. PCT/EP2016/080948 dated Feb. 15, 2017.

* cited by examiner

*Primary Examiner* — Medhanit W Bahta
(74) *Attorney, Agent, or Firm* — NK Patent Law

(57) ABSTRACT

The present invention concerns a method for producing for producing and purifying 2,3,3,3-tetrafluoro-1-propene (1234yf) from a first composition comprising 2,3,3,3-tetrafluoro-1-propene and chloromethane (40), said method comprising the steps of: (a) bringing said first composition into contact with at least one organic extractant in order to form a second composition; (b) extractive distillation of said second composition in order to form (i) a third composition comprising said organic extractant and chloromethane (40); and (ii) a stream comprising 2,3,3,3-tetrafluoro-1-propene (1234yf); (c) recovering and separating said third composition, preferably by distillation, in order to form a stream comprising said organic extractant and a stream comprising chloromethane (40).

12 Claims, 4 Drawing Sheets

(51) Int. Cl.
   *C07C 21/18*      (2006.01)
   *C07C 19/03*      (2006.01)
   *C07C 49/04*        (2006.01)
   *C07C 69/04*        (2006.01)
   *C07C 69/06*        (2006.01)
   *C07C 43/14*        (2006.01)
   *C07C 211/20*       (2006.01)
   *C07C 69/14*        (2006.01)
   *C07C 211/03*       (2006.01)
   *C07C 43/10*        (2006.01)
   *C07C 211/09*       (2006.01)
   *C07C 211/21*       (2006.01)
   *C07C 211/35*       (2006.01)
   *C07C 47/02*        (2006.01)
   *C07C 31/02*        (2006.01)
   *C09K 5/04*         (2006.01)

(52) U.S. Cl.
   CPC ............. *C07C 31/02* (2013.01); *C07C 43/10* (2013.01); *C07C 43/14* (2013.01); *C07C 47/02* (2013.01); *C07C 49/04* (2013.01); *C07C 69/04* (2013.01); *C07C 69/06* (2013.01); *C07C 69/14* (2013.01); *C07C 211/03* (2013.01); *C07C 211/09* (2013.01); *C07C 211/20* (2013.01); *C07C 211/21* (2013.01); *C07C 211/35* (2013.01); *C09K 5/045* (2013.01); *C09K 2205/126* (2013.01)

METHOD FOR PRODUCING AND PURIFYING 2,3,3,3-TETRAFLUORO-1-PROPENE

CROSS REFERENCE TO RELATED APPLICATIONS

This application is a U.S. National Stage application of International Application No. PCT/EP2016/080948 filed on Dec. 14, 2016, which claims the benefit of French Patent Application No. 1563167 filed on Dec. 23, 2015, the entire content of all of which is incorporated by reference herein.

TECHNICAL FIELD OF THE INVENTION

The invention relates to a process for purifying 2,3,3,3-tetrafluoro-1-propene. The invention also relates to a process for producing and purifying 2,3,3,3-tetrafluoro-1-propene.

TECHNOLOGICAL BACKGROUND OF THE INVENTION

Hydrofluorocarbons (HFCs) and in particular hydrofluoroolefins (HFOs), such as 2,3,3,3-tetrafluoro-1-propene (HFO-1234yf), are compounds known for their properties as coolants, heat-transfer fluids, extinguishers, propellants, foaming agents, swelling agents, gaseous dielectrics, polymerization medium or monomer, support fluids, agents for abrasives, drying agents and fluids for power production units. HFOs have been identified as desirable alternatives to HCFC on account of their low ODP (ozone depletion potential) and GWP (global warming potential) values.

Most of the processes for manufacturing hydrofluoroolefins involve a fluorination and/or dehydrohalogenation reaction. These reactions are performed in the gas phase and generate impurities which consequently need to be removed to obtain the desired compound in a sufficient degree of purity for the targeted applications.

For example, in the context of producing 2,3,3,3-tetrafluoro-1-propene (HFO-1234yf), the presence of impurities such as 1-chloro-3,3,3-trifluoro-1-propene (1233zd), 1,3,3,3-tetrafluoro-1-propene (1234ze) and 1,1,1,3,3-pentafluoropropane (245fa) is observed. These impurities are isomers of the main compounds that are desired to be obtained via the process for producing 2,3,3,3-tetrafluoro-1-propene, besides the latter, i.e. 2-chloro-3,3,3-trifluoro-1-propene (1233xf) and 1,1,1,2,2-pentafluoropropane (245cb). Given the respective boiling points of 1-chloro-3,3,3-trifluoro-1-propene (1233zd), 1,3,3,3-tetrafluoro-1-propene (1234ze) and 1,1,1,3,3-pentafluoropropane (245fa), they may accumulate in the reactor and thus prevent the formation of the products of interest.

Purification of this type of reaction mixture may be performed via various techniques known from the prior art, for instance distillation. However, when the compounds to be purified have boiling points that are too close or when they form azeotropic or quasi-azeotropic compositions, distillation is not an efficient process. Extractive distillation processes have thus been described.

EP 0 864 554 discloses a process for purifying a mixture comprising 1,1,1,3,3-pentafluoropropane (245fa) and 1-chloro-3,3,3-trifluoro-trans-1-propene (1233zd) by distillation in the presence of a solvent with a boiling point of greater than that of 1-chloro-3,3,3-trifluoro-trans-1-propene.

WO 03/068716 discloses a process for recovering pentafluoroethane from a mixture comprising pentafluoroethane and chloropentafluoroethane by distillation in the presence of hexafluoropropene.

WO 98/19982 also discloses a process for purifying 1,1-difluoroethane by extractive distillation. The process consists in placing an extracting agent in contact with a mixture of 1,1-difluoroethane and vinyl chloride. The extracting agent is chosen from hydrocarbons, alcohols and chlorocarbons with a boiling point of between 10° C. and 120° C. US2015/291490 also discloses a process for separation between 2,3,3,3-tetrafluoro-1-propene and chloromethane (40).

As mentioned by WO 98/19982, the selection of the extracting agent may prove to be complex depending on the products to be separated. There is thus still a need to develop a particular process for purifying 2,3,3,3-tetrafluoro-1-propene.

SUMMARY OF THE INVENTION

In a process for producing 2,3,3,3-tetrafluoro-1-propene, the choice of particular operating conditions makes it possible to promote the presence of certain impurities or of isomers thereof. The presence of impurities such as 1,3,3,3-tetrafluoro-1-propene (1234ze) may be observed, as may that of 1-chloro-3,3,3-trifluoro-1-propene (1233zd) and 1,1,1,3,3-pentafluoropropane (245fa). These impurities may derive from side reactions induced by intermediate compounds produced during the production of 2,3,3,3-tetrafluoro-1-propene, and may have physical properties such that the removal thereof may prove to be complex. The present invention allows the production of 2,3,3,3-tetrafluoro-1-propene in improved purity.

According to a first aspect, the present invention provides a process for purifying 2,3,3,3-tetrafluoro-1-propene (1234yf) using a first composition comprising 2,3,3,3-tetrafluoro-1-propene and chloromethane (40), said process comprising the steps of:
a) placing said first composition in contact with at least one organic extracting agent to form a second composition;
b) extractive distillation of said second composition to form:
  i) a third composition comprising said organic extracting agent and chloromethane (40); and
  ii) a stream comprising 2,3,3,3-tetrafluoro-1-propene (1234yf)
c) recovery and separation of said third composition, preferably by distillation, to form a stream comprising said organic extracting agent and a stream comprising chloromethane (40); preferably, the stream comprising said organic extracting agent is recycled into step a).

Preferably, the stream comprising 2,3,3,3-tetrafluoro-1-propene formed in step b) is recovered. This stream may be optionally purified to achieve a degree of purity suitable for particular commercial specifications.

According to a preferred embodiment, said first composition, said second composition and said third composition also comprise trans-1,3,3,3-tetrafluoro-1-propene (1234ze-E); step c) being the recovery and separation of said third composition, preferably by distillation, to form, on the one hand, a stream comprising said organic extracting agent and, on the other hand, a stream comprising chloroethane (40) and trans-1,3,3,3-tetrafluoro-1-propene (1234ze-E).

According to a preferred embodiment, said organic extracting agent is a solvent chosen from the group consisting of hydrocarbons, halohydrocarbons, alcohol, ketone, amine, ester, ether, aldehyde, nitrile, carbonate, thioalkyl, amide and heterocycle; or the organic extracting agent is difluorodiethylsilane or triethylfluorosilane; preferably from the group consisting of ketone, amine, ester, ether, alcohol, heterocycle and aldehyde.

According to a preferred embodiment, said organic extracting agent may have a boiling point of between 10 and 150° C.

According to a preferred embodiment, said organic extracting agent has a separation factor $S_{1,2}$ of greater than or equal to 1.1, said separation factor being calculated by the formula $S_{1,2}=(\gamma_{1,S}*P1)/(\gamma_{2,S}*P2)$ in which $\gamma_{1,S}$ represents the activity coefficient of 2,3,3,3-tetrafluoro-1-propene in said organic extracting agent at infinite dilution;

P1 represents the saturating vapor pressure of 2,3,3,3-tetrafluoro-1-propene;

$\gamma_{2,S}$ represents the activity coefficient of chloromethane (40) in said organic extracting agent at infinite dilution;

P2 represents the saturating vapor pressure of chloromethane (40);

advantageously, the separation factor is greater than or equal to 1.2, preferably greater than or equal to 1.4, more preferentially greater than or equal to 1.6, in particular greater than or equal to 1.8, more particularly greater than or equal to 2.0.

According to a preferred embodiment, said organic extracting agent has an absorption capacity $C_{2,S}$ of greater than or equal to 0.20, said absorption capacity being calculated by the formula $C_{2,S}=1/(\gamma_{2,S})$ in which $\gamma_{2,S}$ represents the activity coefficient of chloromethane (40); advantageously, the absorption capacity $C_{2,S}$ is greater than or equal to 0.40, preferably greater than or equal to 0.50, more preferentially greater than or equal to 0.60, in particular greater than or equal to 0.70 and more particularly greater than or equal to 0.80.

According to a preferred embodiment, said organic extracting agent may be chosen so as also to have a particular separation factor and absorption capacity with respect to trans-1,3,3,3-tetrafluoro-1-propene (1234ze-E). This may make it possible to promote the separation between 2,3,3,3-tetrafluoro-1-propene (1234yf) and trans-1,3,3,3-tetrafluoro-1-propene (1234ze-E) if the latter is present in said first composition to be purified. Thus, said organic extracting agent has a separation factor $S_{1,2}$ of greater than or equal to 1.1, said separation factor being calculated by the formula $S_{1,2}=(\gamma_{1,S}*P1)/(\gamma_{2,S}*P2)$ in which $\gamma_{1,S}$ represents the activity coefficient of 2,3,3,3-tetrafluoro-1-propene in said organic extracting agent at infinite dilution;

P1 represents the saturating vapor pressure of 2,3,3,3-tetrafluoro-1-propene;

$\gamma_{2,S}$ represents the activity coefficient of trans-1,3,3,3-tetrafluoro-1-propene (1234ze-E) in said organic extracting agent at infinite dilution;

P2 represents the saturating vapor pressure of trans-1,3,3,3-tetrafluoro-1-propene (1234ze-E); advantageously, the separation factor is greater than or equal to 1.2, preferably greater than or equal to 1.4, more preferentially greater than or equal to 1.6, in particular greater than or equal to 1.8, more particularly greater than or equal to 2.0;

and, preferably, said organic extracting agent has an absorption capacity $C_{2,S}$ of greater than or equal to 0.20, said absorption capacity being calculated by the formula $C_{2,S}=1/(\gamma_{2,S})$ in which $\gamma_{2,S}$ represents the activity coefficient of trans-1,3,3,3-tetrafluoro-1-propene (1234ze-E); advantageously, the absorption capacity $C_{2,S}$ is greater than or equal to 0.40, preferably greater than or equal to 0.50, more preferentially greater than or equal to 0.60, in particular greater than or equal to 0.70 and more particularly greater than or equal to 0.80.

According to a preferred embodiment, said first composition is an azeotropic or quasi-azeotropic composition comprising 2,3,3,3-tetrafluoro-1-propene, chloromethane (40) and trans-1,3,3,3-tetrafluoro-1-propene (1234ze-E).

According to a preferred embodiment, said organic extracting agent is chosen from the group consisting of methyl formate, -methoxy-1-propene, ethoxyethene, propanone, methyl acetate, isobutanal, isopropyl formate, ethyl acetate, butanone, n-propyl formate, 1,2-dimethoxyethane, isopropyl acetate, 1-methoxy-2-propanamine, 2-methoxyethanamine, 2-methylbutanal, tert-butyl acetate, ethyl propionate, dioxane, 3-pentanone, 2-pentanone, 2-methoxy-1-propanamine, trimethoxymethane, 1,3-dioxane, 3,3-dimethyl-2-butanone, 2-ethoxyethanamine, sec-butyl acetate, n-methyl-1,2-ethanediamine, 4-methyl-2-pentanone, 1,2-diaminoethane, butyronitrile, 1-methoxy-2-propanol, 1,2-propanediamine, 2,6-dimethyl-5-heptenal, 1-(dimethylamino)-2-propanol, diethyl carbonate, n-butyl acetate, 2-hexanone, n-ethylethylenediamine, 5-hexen-2-one, 2-methylpyridine, 2-methoxy-1-propanol, 1-ethoxy-2-propanol, hexanal, 2-(dimethylamino)ethanol, 2-methylpyrazine, 2-ethoxy-1-propanol, 1,3-propanediamine, valeronitrile, 2,6-dimethylpyridine, 4-methyl-2-hexanone, 1-methoxy-2-acetoxypropane, 4-methylpyridine, 2,6-dimethylmorpholine, methyl hexanoate, 2-propoxyethanol and 1-propoxy-2-propanol; advantageously methyl formate, ethoxyethene, propanone, methyl acetate, isobutanal, isopropyl formate, ethyl acetate, butanone, isopropyl acetate, 2-methoxyethanamine, tert-butyl acetate, dioxane, 3-pentanone, 2-pentanone, 1,3-dioxane, 3,3-dimethyl-2-butanone, sec-butyl acetate, 4-methyl-2-pentanone, 1,2-diaminoethane, 1-methoxy-2-propanol, 1,2-propanediamine, diethyl carbonate, n-butyl acetate, 2-methoxy-1-propanol, 1-ethoxy-2-propanol and hexanal; preferably methyl formate, propanone, butanone, isopropyl acetate, 2-methoxyethanamine, tert-butyl acetate, dioxane, 1,3-dioxane, sec-butyl acetate, 1,2-diaminoethane, 1-methoxy-2-propanol, 1,2-propanediamine, n-butyl acetate, 2-methoxy-1-propanol, 1-ethoxy-2-propanol and hexanal; in particular methyl formate, isopropyl acetate, 2-methoxyethanamine, tert-butyl acetate, dioxane, 1,3-dioxane, sec-butyl acetate, 1,2-diaminoethane, 1-methoxy-2-propanol, 1,2-propanediamine, n-butyl acetate, 2-methoxy-1-propanol, 1-ethoxy-2-propanol and hexanal.

According to a preferred embodiment, the stream comprising 2,3,3,3-tetrafluoro-1-propene formed in step b) is recovered and is free of chloromethane (40). The term "free of" means that the stream comprising 2,3,3,3-tetrafluoro-1-propene comprises less than 50 ppm, advantageously less than 20 ppm and preferably less than 10 ppm of the compound under consideration on the basis of the total weight of the stream.

According to a preferred embodiment, said process may also comprise, prior to step a), the following steps:

i') use or provision of a composition comprising 2,3,3,3-tetrafluoro-1-propene, impurities with a boiling point below the boiling point of 2,3,3,3-tetrafluoro-1-propene, chloromethane (40) and optionally heavy impurities and/or trans-1,3,3,3-tetrafluoro-1-propene (1234ze-E); preferably use or provision of a composition comprising 2,3,3,3-tetrafluoro-1-propene, impurities with a boiling point below the bonding point of 2,3,3,3-tetrafluoro-1-propene, chloromethane (40), trans-1,3,3,3-tetrafluoro-1-propene (1234ze-E) and optionally heavy impurities;

ii') distillation of said composition from step i) to remove, at the top of the column, impurities with a boiling point below the boiling point of 2,3,3,3-tetrafluoro-1-propene and to form a first stream comprising 2,3,3,3-tetrafluoro-1-propene, chloromethane (40) and optionally or not heavy impurities and/or trans-1,3,3,3-tetrafluoro-1-propene (1234ze-E), recovered at the bottom of the distillation column; preferably, the distillation of said composition from step i) to remove, at the top of the column, impurities with a boiling point below the boiling point of 2,3,3,3-tetrafluoro-1-propene and to form a first stream comprising 2,3,3,3-tetrafluoro-1-propene, chloromethane (40), trans-1,3,3,3-tetrafluoro-1-propene (1234ze-E) and optionally or not heavy impurities, recovered at the bottom of the distillation column;

iii') optionally or not, distillation of said first stream recovered at the bottom of the distillation column in step ii') to recover, at the top of the column, a second stream comprising 2,3,3,3-tetrafluoro-1-propene, chloromethane (40) and optionally or not trans-1,3,3,3-tetrafluoro-1-propene (1234ze-E); and, at the bottom of the distillation column, a stream comprising the heavy impurities; preferably, the second stream comprises 2,3,3,3-tetrafluoro-1-propene, chloromethane (40) and trans-1,3,3,3-tetrafluoro-1-propene (1234ze-E);

said at first stream recovered in step ii') or said second stream recovered in step iii') corresponds to said first composition used in step a).

According to a second aspect of the present invention, a process for producing and purifying 2,3,3,3-tetrafluoro-1-propene is provided. Said process comprises the steps of:

A) fluorination in the presence of a catalyst of a compound of formula $CX(Y)_2$—$CX(Y)_m$—$CH_mXY$ (I) in which X and Y independently represent H, F or Cl and m=0 or 1; and/or fluorination in the presence of a catalyst of a compound of formula $(CX_nY_{3-n})CH_pX_{1-p}CH_mX_{2-m}$ (II) in which X is, independently of each other, Cl, F, I or Br; Y is, independently of each other, H, Cl, F, I or Br; n is 1, 2 or 3; and m is 0, 1 or 2; and p is 0 or 1;

B) recovery of a stream comprising 2,3,3,3-tetrafluoro-1-propene, chloromethane (40) and optionally or not trans-1,3,3,3-tetrafluoro-1-propene (1234ze-E);

C) implementation of the process for purifying 2,3,3,3-tetrafluoro-1-propene according to the present invention using the stream recovered in step B).

According to a third aspect, the present invention provides a composition comprising 2,3,3,3-tetrafluoropropene, an organic extracting agent, chloromethane (40) and trans-1,3,3,3-tetrafluoro-1-propene (1234ze-E); said organic extracting agent having a separation factor $S_{1,2}$ of greater than 1.6, said separation factor being calculated by the formula $S_{1,2}=(\gamma_{1,S}*P1)/(\gamma_{2,S}*P2)$ in which $\gamma_{1,S}$ represents the activity coefficient of 2,3,3,3-tetrafluoropropene in said organic extracting agent at infinite dilution, P1 represents the saturating vapor pressure of 2,3,3,3-tetrafluoropropene, $\gamma_{2,S}$ represents the activity coefficient of chloromethane (40) in said organic extracting agent at infinite dilution, P2 represents the saturating vapor pressure of chloromethane (40); and preferably, said organic extracting agent has an absorption capacity $C_{2,S}$ of greater than or equal to 0.8, said absorption capacity being calculated by the formula $C_{2,S}=1/$ ($\gamma_{2,S}$) in which $\gamma_{2,S}$ represents the activity coefficient of chloromethane (40) in said organic extracting agent at infinite dilution; and a separation factor $S_{1,2}$ of greater than 1.6, said separation factor being calculated by the formula $S_{1,2}=(\gamma_{1,S}*P1)/(\gamma_{2,S}*P2)$ in which $\gamma_{1,S}$ represents the activity coefficient of 2,3,3,3-tetrafluoropropene in said organic extracting agent at infinite dilution, P1 represents the saturating vapor pressure of 2,3,3,3-tetrafluoropropene, $\gamma_{2,S}$ represents the activity coefficient of trans-1,3,3,3-tetrafluoro-1-propene (1234ze-E) in said organic extracting agent at infinite dilution, P2 represents the saturating vapor pressure of trans-1,3,3,3-tetrafluoro-1-propene (1234ze-E); and preferably, said organic extracting agent has an absorption capacity $C_{2,S}$ of greater than or equal to 0.8, said absorption capacity being calculated by the formula $C_{2,S}=1/(\gamma_{2,S})$ in which $\gamma_{2,S}$ represents the activity coefficient of trans-1,3,3,3-tetrafluoro-1-propene (1234ze-E) in said organic extracting agent at infinite dilution.

According to a preferred embodiment, in said composition, the organic extracting agent is chosen from the group consisting of methyl formate, ethoxyethene, propanone, methyl acetate, isobutanal, isopropyl formate, ethyl acetate, butanone, isopropyl acetate, 2-methoxyethanamine, tert-butyl acetate, dioxane, 3-pentanone, 2-pentanone, 1,3-dioxane, 3,3-dimethyl-2-butanone, sec-butyl acetate, 4-methyl-2-pentanone, 1,2-diaminoethane, 1-methoxy-2-propanol, 1,2-propanediamine, diethyl carbonate, n-butyl acetate, 2-methoxy-1-propanol, 1-ethoxy-2-propanol and hexanal; preferably methyl formate, propanone, butanone, isopropyl acetate, 2-methoxyethanamine, tert-butyl acetate, dioxane, 1,3-dioxane, sec-butyl acetate, 1,2-diaminoethane, 1-methoxy-2-propanol, 1,2-propanediamine, n-butyl acetate, 2-methoxy-1-propanol, 1-ethoxy-2-propanol and hexanal; in particular methyl formate, isopropyl acetate, 2-methoxyethanamine, tert-butyl acetate, dioxane, 1,3-dioxane, sec-butyl acetate, 1,2-diaminoethane, 1-methoxy-2-propanol, 1,2-propanediamine, n-butyl acetate, 2-methoxy-1-propanol, 1-ethoxy-2-propanol and hexanal.

According to a preferred embodiment, said composition comprises between 75% and 99.99% by weight of 2,3,3,3-tetrafluoro-1-propene, between 0.01% and 25% by weight of trans-1,3,3,3-tetrafluoro-1-propene (1234ze-E) and less than 1% by weight of chloromethane (40) relative to the total weight of the composition.

DETAILED DESCRIPTION OF THE INVENTION

Figure 1A:
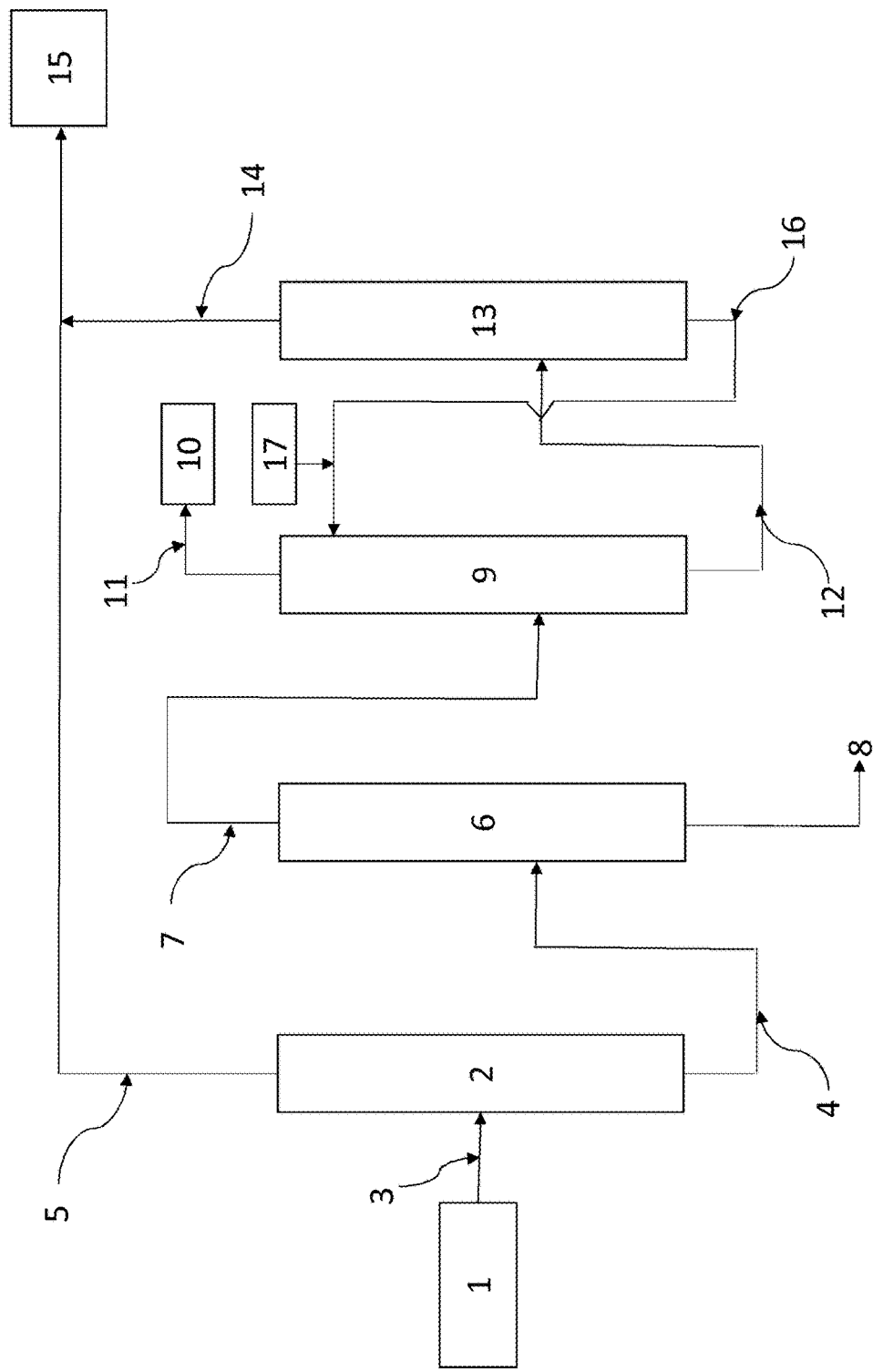
FIGS. 1a-c schematically represent a device for performing a process for purifying 2,3,3,3-tetrafluoro-1-propene according to a particular embodiment of the present invention.

The term "hydrocarbon" as used herein refers to linear or branched $C_1$-$C_{20}$ alkane, $C_3$-$C_{20}$ cycloalkane, $C_2$-$C_{20}$ alkene, $C_3$-$C_{20}$ cycloalkene or $C_6$-$C_{18}$ arene compounds. For example, the term "alkane" refers to compounds of formula $C_nH_{2n+2}$ in which n is between 1 and 20. The term "$C_1$-$C_{20}$ alkane" includes, for example, pentane, hexane, heptane, octane, nonane and decane, or isomers thereof. The term "$C_2$-$C_{20}$ alkene" refers to hydrocarbon-based compounds comprising one or more carbon-carbon double bonds and comprising from 2 to 20 carbon atoms. The term "$C_3$-$C_{20}$ cycloalkane" refers to a saturated hydrocarbon-based ring comprising from 3 to 20 carbon atoms. The term "$C_6$-$C_{18}$ aryl" refers to cyclic and aromatic hydrocarbon-based compounds comprising from 6 to 18 carbon atoms. The term "$C_3$-$C_{20}$ cycloalkene" refers to cyclic hydrocarbon-based compounds comprising from 3 to 20 carbon atoms and comprising one or more carbon-carbon double bonds.

The term "alkyl" denotes a monovalent radical derived from a linear or branched alkane, comprising from 1 to 20 carbon atoms. The term "cycloalkyl" denotes a monovalent radical derived from a cycloalkane, comprising from 3 to 20 carbon atoms. The term "aryl" denotes a monovalent radical derived from an arene, comprising from 6 to 18 carbon atoms. The term "alkenyl" denotes a monovalent radical of 2 to 20 carbon atoms and at least one carbon-carbon double bond. The term "alkynyl" denotes a monovalent radical of 2 to 20 carbon atoms and at least one carbon-carbon triple bond. The term "halogen" refers to an —F, —Cl, —Br or —I group. The term "cycloalkenyl" refers to a monovalent radical derived from a cycloalkene comprising from 3 to 20 carbon atoms. The $C_1$-$C_{20}$ alkyl, $C_2$-$C_{20}$ alkenyl, $C_2$-$C_{20}$ alkynyl, $C_3$-$C_{20}$ cycloalkyl, $C_3$-$C_{20}$ cycloalkenyl and $C_6$-$C_{18}$ aryl substituents may be optionally substituted with one or more —OH, halogen, —NR$^a$C(O)R$^b$, —C(O)NR$^a$R$^b$—CN, —NO$_2$, —NR$^a$R$^b$, —OR$^a$, —SR$^a$, —CO$_2$R$^a$, —OC(O)OR$^a$, —OC(O)R$^a$, —C(O)H or —C(O)R$^a$ substituents in which R$^a$ and R$^b$ are, independently of each other, hydrogen, unsubstituted $C_1$-$C_{20}$ alkyl, unsubstituted $C_2$-$C_{20}$ alkenyl, unsubstituted $C_2$-$C_{20}$ alkynyl, unsubstituted $C_3$-$C_{20}$ cycloalkyl, unsubstituted $C_3$-$C_{20}$ cycloalkenyl or unsubstituted $C_6$-$C_{18}$ aryl. In the substituents —NR$^a$R$^b$, —NR$^a$C(O)R$^b$, —C(O)NR$^a$R$^b$, R$^a$ and R$^b$ may form, with the nitrogen atom or with the functional group to which they are attached, a saturated or unsaturated, aromatic or non-aromatic, 4- to 10-membered heterocycle.

The term "halohydrocarbons" refers to compounds of formula R$^a$X in which R$^a$ is chosen from $C_1$-$C_{20}$ alkyl, $C_2$-$C_{20}$ alkenyl, $C_2$-$C_{20}$ alkynyl, $C_3$-$C_{20}$ cycloalkyl, $C_3$-$C_{20}$ cycloalkenyl and $C_6$-$C_{18}$ aryl and X represents a chlorine, fluorine, bromine or iodine atom. The $C_1$-$C_{20}$ alkyl, $C_2$-$C_{20}$ alkenyl, $C_2$-$C_{20}$ alkynyl, $C_3$-$C_{20}$cycloalkenyl and $C_6$-$C_{18}$ aryl substituents may cycloalkyl, $C_3$-$C_{20}$ be optionally substituted with one or more —OH, halogen, —NR$^a$C(O)R$^b$, —C(O)NR$^a$R$^b$—CN, —NO$_2$, —NR$^a$R$^b$, —OR$^a$, —SR$^a$, —CO$_2$R$^a$, —OC(O)OR$^a$, —OC(O)R$^a$, —C(O)H or —C(O)R$^a$ substituents in which R$^a$ and R$^b$ are as defined above.

The term "alcohol" refers to hydrocarbons or halohydrocarbons as defined above in which at least one hydrogen atom is replaced with a hydroxyl group —OH.

The term "ketone" refers to hydrocarbons comprising at least one or more carbonyl functional groups R$^c$—C(O)—R$^d$ in which R$^c$ and R$^d$ are, independently of each other, a $C_1$-$C_{20}$ alkyl, $C_2$-$C_{20}$ alkenyl, $C_2$-$C_{20}$ alkynyl, $C_3$-$C_{20}$ cycloalkyl, $C_3$-$C_{20}$ cycloalkenyl or $C_6$-$C_{18}$ aryl and may be optionally substituted with one or more —OH, halogen, —NR$^a$C(O)R$^b$, —C(O)NR$^a$R$^b$—CN, —NO$_2$, —NR$^a$R$^b$, —OR$^a$, —SR$^a$, —CO$_2$R$^a$, —OC(O)OR$^a$, —OC(O)R$^a$, —C(O)H, —C(O)R$^a$ substituents in which R$^a$ and R$^b$ are as defined above, R$^c$ and R$^d$ possibly being linked together to form, with the carbonyl group to which they are attached, a 4- to 10-membered and preferably 4- to 7-membered cyclic ketone. The cyclic ketone may also comprise one or more carbon-carbon double bonds. The cyclic ketone may also be optionally substituted with one or more substituents as defined above.

The term "amine" refers to hydrocarbons comprising at least one or more amine functional groups —NR$^c$R$^d$ in which R$^c$ and R$^d$ are as defined above, R$^c$ and R$^d$ possibly being linked together to form, with the nitrogen atom to which they are attached, a 4- to 10-membered aromatic or non-aromatic heterocycle.

The term "esters" refers to compounds of formula R$^c$—C(O)—O—R$^d$ in which R$^c$ and R$^d$ are as defined above, R$^c$ and R$^d$ possibly being linked together to form, with the ester group, a ring comprising from 4 to 20 carbon atoms.

The term "ether" refers to compounds of formula R$^c$—O—R$^d$ in which R$^c$ and R$^d$ are as defined above, R$^c$ and R$^d$ possibly being linked together to form, with the oxygen atom to which they are attached, a heterocycle comprising from 4 to 20 carbon atoms.

The term "aldehyde" refers to compounds comprising at least one or more —C(O)—H functional groups.

The term "nitrile" refers to compounds comprising at least one or more —CN functional groups.

The term "carbonate" refers to compounds of formula R$^c$—O—C(O)—O—R$^d$ in which R$^c$ and R$^d$ are as defined above.

The term "thioalkyl" refers to compounds of formula R$^c$SR$^d$ in which R$^c$ and R$^d$ are as defined above.

The term "amide" relates to compounds of formula R$^c$C(O)NR$^e$R$^d$ in which R$^c$ and R$^d$ are as defined above, R$^e$ being defined by the same substituents as R$^c$; R$^c$ and R$^d$ possibly being linked together to form, with the amide group —C(O)N— to which they are attached, a 4- to 10-membered and preferably 4- to 7-membered cyclic amide. The cyclic amide may also comprise one or more carbon-carbon double bonds. The cyclic amide may also be optionally substituted with one or more substituents as defined above.

The term "heterocycle" denotes a 4- to 10-membered carbon-based ring, at least one of the ring members of which is a heteroatom chosen from the group consisting of O, S, P and N. The ring may comprise one or more carbon-carbon double bonds or one or more carbon-heteroatom double bonds or one or more heteroatoms-heteroatom double bonds. Preferably, the heterocycle may comprise 1, 2, 3, 4 or 5 heteroatoms as defined above. In particular, the heterocycle may comprise 1, 2 or 3 heteroatoms chosen from oxygen, nitrogen and sulfur. Preferably, the heterocycle may be a 4- to 6-membered carbon-based ring, 1, 2 or 3 ring members of which are heteroatoms chosen from O and N. The heterocycle may be optionally substituted with one or more substituents chosen from —OH, halogen, —NR$^a$C(O)R$^b$, —C(O)NR$^a$R$^b$—CN, —NO$_2$, —NR$^a$R$^b$, —OR$^a$, —SR$^a$, —CO$_2$R$^a$, —OC(O)OR$^a$, —OC(O)R$^a$, —C(O)H and —C(O)R$^a$ in which R$^a$ and R$^b$ are as defined above.

The term "azeotropic composition" denotes a liquid mixture of two or more compounds which behave like a single substance, and which boils at a fixed temperature maintaining a composition in the liquid phase identical to that in the gas phase. The term "quasi-azeotropic composition" denotes a liquid mixture of two or more compounds having a constant boiling point or which has a tendency not to fractionate when it is subjected to boiling or to evaporation. The term "organic extracting agent" refers to a compound comprising at least one carbon atom.

According to a first aspect, the invention relates to a process for purifying 2,3,3,3-tetrafluoro-1-propene (1234yf). The purification process is performed starting with a first composition comprising 2,3,3,3-tetrafluoro-1-propene and chloromethane (40).

Preferably, said process comprises the steps of:
a) placing said first composition in contact with at least one organic extracting agent to form a second composition;
b) extractive distillation of said second composition to form:
   i) a third composition comprising said organic extracting agent and chloromethane (40); and
   ii) a stream comprising 2,3,3,3-tetrafluoro-1-propene;
c) recovery and separation of said third composition, preferably by distillation, to form a stream comprising said organic extracting agent and a stream comprising chloromethane (40).

According to a preferred embodiment, the stream comprising said organic extracting agent is recycled into step a) of the present process.

According to a preferred embodiment, said first composition may comprise trans-1,3,3,3-tetrafluoro-1-propene (1234ze-E). Thus, said second composition may comprise trans-1,3,3,3-tetrafluoro-1-propene (1234ze-E). Said third composition may thus comprise trans-1,3,3,3-tetrafluoro-1-propene (1234ze-E). Advantageously, step c) of the present process may consist in recovering and separating out said third composition, preferably by distillation, to form, on the one hand, a stream comprising said organic extract agent and, on the other hand, a stream comprising chloromethane (40) and trans-1,3,3,3-tetrafluoro-1-propene (1234ze-E).

Thus, the present invention may be a process for purifying 2,3,3,3-tetrafluoro-1-propene (1234yf) using a first composition comprising 2,3,3,3-tetrafluoro-1-propene, chloromethane (40) and trans-1,3,3,3-tetrafluoro-1-propene (1234ze-E), said process comprising the steps of:
a) placing said first composition in contact with at least one organic extracting agent to form a second composition;
b) extractive distillation of said second composition to form:
   i) a third composition comprising said organic extracting agent, trans-1,3,3,3-tetrafluoro-1-propene (1234ze-E) and chloromethane (40); and
   ii) a stream comprising 2,3,3,3-tetrafluoro-1-propene (1234yf);
c) recovery and separation of said third composition, preferably by distillation, to form, on the one hand, a stream comprising said organic extracting agent and, on the other hand, a stream comprising chloromethane (40) and trans-1,3,3,3-tetrafluoro-1-propene (1234ze-E); preferably, the stream comprising said organic extracting agent is recycled into step a).

Said first composition may comprise between 75% and 99.99% by weight of 2,3,3,3-tetrafluoro-1-propene relative to the total weight of the first composition, advantageously between 80% and 99.9% by weight, preferably between 85% and 99.8% and in particular between 90% and 99.5% by weight of 2,3,3,3-tetrafluoro-1-propene relative to the total weight of the first composition.

When it contains same, said first composition may comprise less than 1% by weight of chloromethane (40) relative to the total weight of the first composition, advantageously between 1 and 5000 ppm by weight, preferably between 1 and 2000 ppm and in particular between 10 and 1500 ppm by weight of chloromethane (40) relative to the total weight of the first composition.

When it contains same, said first composition may comprise between 0.01% and 25% by weight of trans-1,3,3,3-tetrafluoro-1-propene (1234ze-E) relative to the total weight of the first composition, advantageously between 0.1% and 20% by weight, preferably between 0.2% and 15%, in particular between 0.5% and 10% by weight and more particularly between 3% and 10% by weight of trans-1,3,3,3-tetrafluoro-1-propene (1234ze-E) relative to the total weight of the first composition.

According to a preferred embodiment, said organic extracting agent may be a solvent chosen from the group consisting of hydrocarbons, halohydrocarbon, alcohol, ketone, amine, ester, ether, aldehyde, nitrile, carbonate, thioalkyl, amide and heterocycle. Alternatively, said organic extracting agent may be difluorodiethylsilane or triethylfluorosilane. Preferably, said organic extracting agent may be chosen from the group consisting of ketone, amine, ester, ether, alcohol, heterocycle and aldehyde. Preferably, the heterocycle may be a 4- to 6-membered carbon-based ring, 1, 2 or 3 ring members of which are heteroatoms chosen from O and N, preferably O.

When the first composition contains trans-1,3,3,3-tetrafluoro-1-propene (1234ze-E), the organic extracting agent may be chosen to allow separation between said compound and 2,3,3,3-tetrafluoro-1-propene (1234yf). Thus, the present process may allow separation between, on the one hand, 2,3,3,3-tetrafluoro-1-propene (1234yf) and, on the other hand, chloromethane (40) and trans-1,3,3,3-tetrafluoro-1-propene (1234ze-E).

Preferably, the hydrocarbons are chosen from the group consisting of 2,2-dimethylbutane, 3-methylpentane, 2,4-dimethylpentane, cyclohexane, cyclohexene, methylcyclohexane, 2,4,4-trimethyl-1-pentene, 2,2,4-trimethyl-2-pentene, 1-methylcyclohexene, toluene, 2,3-dimethylhexane, ethylcyclohexane, ethylbenzene, 1,4-dimethylbenzene, 1,3-dimethylbenzene, 1,2,3-trimethylcyclohexane, 1,2-dimethylbenzene and styrene.

Preferably, the halohydrocarbons are chosen from the group consisting of chloroethane, bromofluoromethane, 1-bromo-1,2-difluoroethylene, trichlorofluoromethane, 1-chloro-1,1-difluoropropane, 1,1,1-trifluoro-2-bromoethane, 1,1-dichloro-2,2,2-trifluoroethane, 1,2-dichloro-1,1,2-trifluoroethane, 1,1-dichloroethylene, 2-chloro-2-fluoropropane, 1-chloro-2,2-difluoroethane, 2-chloropropane, bromoethane, 2-chloro-1,1,1,3,3-pentafluoropropane, 1-chloro-1,2,2-trifluoropropane, iodomethane, 3-chloropropene, 3-chloro-1,1,1-trifluoropropane, 1,1,1-trichloro-2,2,2-trifluoroethane, 1,2-dichloro-1,2-difluoroethane, 1,1,2-trichloro-1,2,2-trifluoroethane, 1,2-dichloro-1,1,3,3,3-pentafluoropropane, 1-chloro-1,2,2,3-tetrafluoropropane, 2-chloro-2-methylpropane, 3-chloro-1,1,1,3-tetrafluoropropane, 2-chloro-1,1,1,3-tetrafluoropropane, 1,3-dichloro-1,1,2,3,3-pentafluoropropane, 1,2-dichloro-3,3,3-trifluoropropene, 1,3-dichloro-1,1,2,2,3-pentafluoropropane, 2,2-dichloro-1,1,1,3-tetrafluoropropane, 1-chloro-2,2-difluoropropane, 1,1-dichloroethane, 2-bromopropane, 1,1-dichloro-2,2-difluoroethane, 2,2-dichloro-1,1,3,3-tetrafluoropropane, 2,3-dichloro-1,1,1,2-tetrafluoropropane, 1,1-dichloro-1,2,2,3-tetrafluoropropane, 1,3-dichloro-1,1,2,2-tetrafluoropropane, 1,1,1-trichloro-2,2-difluoroethane, 1,2-dichloro-1,2,3,3-tetrafluoropropane, chlorobromomethane, 2-chlorobutane, 1,3-dichloro-1,1,3,3-tetrafluoropropane, 1,3-dichloro-1,2,2,3-tetrafluoropropane, 1,2-dichloro-1,1,2,3-tetrafluoropropane, 3-bromopropene, 2,3-dichloro-1,1,1,3-tetrafluoropropane, 1,1-dichloro-2-fluoroethane, 1-bromopropane, 1,1-difluoro-1,2,2-trichloroethane, 1,1,2-trichloro-1,2-difluoroethane, iodoethane, 2-bromo-2-methylpropane, 1,2-dichloro-1-fluoroethane, 1,1,1-trichloroethane, 1-chloro-3-fluoropropane, 2,3-dichloro-1,1,1-trifluoropropane, tetrachloromethane, 1-chlorobutane, 1,3-dichloro-1,1,2-trifluoropropane, 1,1-dichloro-2,2,3-trifluoropropane, 1,3,3-trichloro-1,1,2,2- tetrafluoropropane, 2-chloro-2-methylbutane, 1,2-dichloroethane, 1,1,1-trichloro-2,2,3,3-tetrafluoropropane, 1,1,3-trichloro-1,2,2,3-tetrafluoropropane, 1,3-dichloro-1,2,2-trifluoropropane, trichloroethene, 1,1-dichloropropane, 1,2-dichloro-2-fluoropropane, 2-iodopropane, dichlorobromomethane, 2-bromobutane, 2,2-difluorotetrachloroethane, 1,1,2,2-tetrachloro-1,2-difluoroethane, 1-fluorohexane, 1,3-dichloro-1,2,3-trifluoropropane, 2,3-dichloro-1-propene, 3-chloropentane, trichloroacetaldehyde, isoamyl chloride, 1,1,1-trichloro-2,2,3-trifluoropropane, 1-chloro-4-fluorobutane, 1-bromo-3-fluoropropane, 1-bromobutane, 1,1,2-trichloro-2-fluoroethane, 1-iodopropane, 1,1,3-trichloro-1,2,2-trifluoropropane, 1,1,3-trichloro-2,2,3-trifluoropropane, cis-1,3-dichloropropene, 2,2-dichlorobutane, bromotrichloromethane, 1,1,1,2-tetrachloro-2-fluoroethane, 1-bromo-2-chloroethane, 2-bromo-2-methylbutane, trans-1,3-dichloropropene, 2-fluorotoluene, 1,1,2-trichloroethane, 1,1,1-trichloro-3-fluoropropane, 3,3,3-trichloro-1-propene, 1-chloro-3,3-dimethylbutane, 1,1,1,2-tetrachloro-3,3,3-trifluoropropane, 2-bromopentane, trichloroacetyl chloride, 2,3-dichlorobutane, 1,1,3,3-tetrachloro-1,2,2-trifluoropropane, 1,1,1,3-tetrachloro-2,2,3-trifluoropropane, 1-bromo-3-methylbutane, 1,3-dichloro-trans-2-butene, 1,3-dichloropropane, tetrachloroethene, 1,2-dibromo-1-fluoroethane, 1,2,2-trichloropropane, 1,2-dichlorobutane, 1,2,2,3-tetrachloro-3,3-difluoropropane, 2,3-dichloro-2-methylbutane, 1-bromopentane, 1,2-dichloro-2-butene, 1-iodobutane, 1,2-dibromoethane, chlorobenzene, 1,1,2-trichloropropane, 1,3-dichlorobutane, pentachlorofluoroethane, 1,2-dibromopropane, 1,2,3-trichloropropene, 1-chloro-3-bromopropane, 1,1,3,3-tetrachloro-1-fluoropropane, 1,1,2,2,3-pentchloro-3,3-difluoropropane, 1,1,2,2-tetrachloroethane, 1,2-dichloropentane and tribromomethane.

Preferably, the alcohols are chosen from the group consisting of 2,2,2-trifluoroethanol, 1,1,1-trifluoro-2-propanol, tert-butanol, 2,2-difluoroethanol, 2-allyloxyethanol, 2-methyl-2-butanol, 2,2,3,3-tetrafluoro-1-propanol, 2,2-dimethyl-1-propanol, 1-methoxy-2-propanol, 1-(dimethylamino)-2-propanol, 3-methyl-3-pentanol, 1-chloro-2-methyl-2-propanol, 4,4,4-trifluorobutanol, 3-fluoropropanol, 2-chloroethanol, 2-methoxyl-propanol, 1-ethoxy-2-propanol, 4-methyl-2-pentanol, 1,2-octanediol, 2-chloro-1-propanol, 2-(dimethylamino)ethanol, 3-hexanol, 2-hexanol, 2-ethoxy-1-propanol, 3,3,4,4,5,5,6,6-octafluoro-1-pentanol, 2,3-dimethylbutanol, 2-ethyl-1-butanol, 2-methyl-1-pentanol, 2-propoxyethanol, 1-propoxy-2-propanol and 2-aminophenol.

Preferably, the ketones are chosen from the group consisting of propanone, butanone, 3-pentanone, 2-pentanone, 3,3-dimethyl-2-butanone, 4-methyl-2-pentanone, 2-hexanone, 5-hexen-2-one and 4-methyl-2-hexanone.

Preferably, the amines are chosen from the group consisting of ethylamine, isopropylamine, ethylmethylamine, 2-amino-2-methylpropane, n-propylamine, isopropylmethylamine, diethylamine, 2-butanamine, n-methylpropylamine, 1-butylamine, diisopropylamine, 3-methyl-2-butanamine, 3-pentylamine, n-methylbutylamine, 1-methoxy-2-propanamine, 2-methoxyethanamine, 2-methoxy-1-propanamine, n-pentylamine, n-methylhydroxylamine, dipropylamine, 2-ethoxyethanamine, n-methyl-1,2-ethanediamine, pyridine, 1,2-diaminoethane, 1,2-propanediamine, 2-ethylbutylamine, n-ethylethylenediamine, 1,1-diethoxy-n,n-dimethylmethanamine, 2-methylpyridine, 4-methyl-2-hexanamine, hexylamine, cyclohexylamine, n-ethyl-2-dimethylaminoethylamine, 1,3-propanediamine, 2-heptanamine, n,n-diethylethylenediamine, 2,6-dimethylpyridine, 4-methylpyridine, n,n'-diethyl-1,2-ethanediamine and dimethylethanolamine.

Preferably, the esters are chosen from the group consisting of methyl formate, methyl acetate, isopropyl formate, ethyl acetate, n-propyl formate, isopropyl acetate, tert-butyl acetate, ethyl propionate, sec-butyl acetate, diethyl carbonate, n-butyl acetate, bromoacetic acid methyl ester and methyl hexanoate.

Preferably, the ethers are chosen from the group consisting of 2,2,2-trifluoroethyl methyl ether, 1,1,2,2-tetrafluoroethyl methyl ether, 2-methoxy-1-propene, diethyl ether, ethoxyethene, dimethoxymethane, methyl cyclopropyl ether, 2-ethoxypropane, methyl t-butyl ether, ethyl 1,1,2,2-tetrafluoroethyl ether, chloromethoxymethane, diisopropyl ether, 2-ethoxy-2-methylpropane, 2-ethoxybutane, 1-methoxy-2-methylbutane, 2,2-dimethoxypropane, 1-ethoxy-2-methylpropane, 1,2-dimethoxyethane, diethoxymethane, di-n-propyl ether, 1-ethoxybutane, 1-methoxypentane, 1,2-dimethoxypropane, isopropyl isobutyl ether, 1,1-diethoxyethane, trimethoxymethane, 1,1-dichloro-2,2-difluoroethyl methyl ether, 2,2-diethoxypropane, isobutyl tert-butyl ether, sec-butyl tert-butyl ether, 1,1-diethoxypropane, 2-methoxyethanol, 2-chloro-1,1-dimethoxyethane, methoxycyclohexane, ethoxyethanol, di-n-butyl ether, 1-ethoxyhexane, 1-methoxy-2-acetoxypropane and 1,1,1-triethoxyethane.

Preferably, the aldehydes are chosen from the group consisting of acetaldehyde, ethanedial, isobutanal, methylglyoxal, 2-methylbutanal, 2,6-dimethyl-5-heptenal and hexanal.

Preferably, the nitriles are chosen from the group consisting of propionitrile, butyronitrile, valeronitrile and (methyleneamino)acetonitrile.

Preferably, the carbonate is diethyl carbonate.

Preferably, the amide is ethanethioamide.

Preferably, the thioalkyls are chosen from the group consisting of ethanethiol, dimethyl sulfide, 2-propanethiol, 4-methoxy-2-methyl-2-butanethiol, tert-butylthiol, 1-propanethiol, thiophene, 2-butanethiol, 2-methyl-1-propanethiol, diethyl sulfide, butanethiol, 3-mercapto-1,2-propanediol, tetrahydrothiophene and 1-pentanethiol.

Preferably, the heterocycles are chosen from the group consisting of furan, 1,2-epoxypropane, dioxane, 1,3-dioxane, piperidine, 1,3,5-trioxane, n-methylmorpholine, 2-methylpyrazine, 1-methylpiperazine, n-ethylmorpholine, 2,6-dimethylmorpholine and 3-furfural.

Said organic extracting agent may be chloroethane, ethylamine, bromofluoromethane, 1-bromo-1,2-difluoroethylene, acetaldehyde, trichlorofluoromethane, 1-chloro-1,1-difluoropropane, 1,1,1-trifluoro-2-bromoethane, 1,1-dichloro-2,2,2-trifluoroethane, 1,2-dichloro-1,1,2-trifluoroethane, 2,2,2-trifluoroethyl methyl ether, 1,1-dichloroethylene, furan, methyl formate, isopropylamine, 1,1,2,2-tetrafluoroethyl methyl ether, 2-methoxy-1-propene, diethyl ether, 1,2-epoxypropane, ethanethiol, 2-chloro-2-fluoropropane, ethoxyethene, 1-chloro-2,2-difluoroethane, ethylmethylamine, dimethyl sulfide, 2-chloropropane, bromoethane, dimethoxymethane, 2-chloro-1,1,1,3,3-pentafluoropropane, 1-chloro-1,2,2-trifluoropropane, iodomethane, 2-amino-2-methylpropane, methyl cyclopropyl ether, 3-chloropropene, 3-chloro-1,1,1-trifluoropropane, 1,1,1-trichloro-2,2,2-trifluoroethane, 1,2-dichloro-1,2-difluoroethane, n-propylamine, 1,1,2-trichloro-1,2,2-trifluoroethane, 2,2-dimethylbutane, isopropylmethylamine, ethanedial, 1,2-dichloro-1,1,3,3-pentafluoropropane, 1-chloro-1,2,2,3-tetrafluoropropane, 2-chloro-2-methylpropane, 3-chloro-1,1,1,3-tetrafluoropropane, 2-chloro-1,1,1,3-tetrafluoropropane, 2-propanethiol, 1,3-dichloro-1,1,2,3,3-pentafluoropropane, 1,2-dichloro-3,3,3-trifluoropropene, 1,3-dichloro-1,1,2,2,3-pentafluoropropane, 2-ethoxypropane, 2,2-dichloro-1,1,1,3- tetrafluoropropane, 1-chloro-2,2-difluoropropane, methyl t-butyl ether, diethylamine, propanone, methyl acetate, 1,1-dichloroethane, ethyl 1,1,2,2-tetrafluoroethyl ether, 4-methoxy-2-methyl-2-butanethiol, 2-bromopropane, chloromethoxymethane, 1,1-dichloro-2,2-difluoroethane, 2,2-dichloro-1,1,3,3-tetrafluoropropane, difluorodiethylsilane, 2-butanamine, 2,3-dichloro-1,1,1,2-tetrafluoropropane, n-methylpropylamine, 3-methylpentane, 1,1-dichloro-1,2,2,3-tetrafluoropropane, tert-butylthiol, isobutanal, 1,3-dichloro-1,1,2,2-tetrafluoropropane, 1,1,1-trichloro-2,2-difluoroethane, 1,2-dichloro-1,2,3,3-tetrafluoropropane, 1-propanethiol, chlorobromomethane, 2-chlorobutane, isopropyl formate, diisopropyl ether, 1,3-dichloro-1,1,3,3-tetrafluoropropane, 1,3-dichloro-1,2,2,3-tetrafluoropropane, 1,2-dichloro-1,1,2,3-tetrafluoropropane, 3-bromopropene, 2,3-dichloro-1,1,1,3-tetrafluoropropane, 1,1-dichloro-2-fluoroethane, 1-bromopropane, 1,1-difluoro-1,2,2-trichloroethane, 1,1,2-trichloro-1,2-difluoroethane, methylglyoxal, iodoethane, 2-ethoxy-2-methylpropane, 2-bromo-2-methylpropane, 1,2-dichloro-1-fluoroethane, 1,1,1-trichloroethane, 2,2,2-trifluoroethanol, 1-chloro-3-fluoropropane, 1,1,1-trifluoro-2-propanol, 2,3-dichloro-1,1,1-trifluoropropane, ethyl acetate, 1-butylamine, 1-chlorobutane, butanone, 2,4-dimethylpentane, cyclohexane, n-propyl formate, 2-ethoxybutane, 2-propanol, tert-butanol, 1,3-dichloro-1,1,2-trifluoropropane, 1-methoxy-2-methylbutane, 1,1-dichloro-2,2,3-trifluoropropane, cyclohexene, 2,2-dimethoxypropane, 1,3,3-trichloro-1,1,2,2-tetrafluoropropane, 2-chloro-2-methylbutane, 1,2-dichloroethane, 1-ethoxy-2-methylpropane, diisopropylamine, thiophene, 2-butanethiol, 1,1,1-trichloro-2,2,3,3-tetrafluoropropane, 1,2-dimethoxyethane, 3-methyl-2-butanamine, 1,1,3-trichloro-1,2,2,3-tetrafluoropropane, 1,3-dichloro-1,2,2-trifluoropropane, diethoxymethane, 1,1-dichloropropane, 2-methyl-1-propanethiol, 1,2-dichloro-2-fluoropropane, isopropyl acetate, 2-iodopropane, di-n-propyl ether, 3-pentylamine, n-methylbutylamine, 2-bromobutane, 2,2-difluorotetrachloroethane, diethyl sulfide, 1-ethoxybutane, 1,1,2,2-tetrachloro-1,2-difluoroethane, 1-fluorohexane, 1-methoxy-2-propanamine, 1,3-dichloro-1,2,3-trifluoropropane, 2,3-dichloro-1-propene, 2-methoxyethanamine, 2,2-difluoroethanol, 2-methylbutanal, tert-butyl acetate, propionitrile, 3-chloropentane, trichloroacetaldehyde, 2-allyloxyethanol, butanethiol, isoamyl chloride, 1-methoxypentane, ethyl propionate, 1,2-dimethoxypropane, isopropyl, isobutyl ether, 1,1,1-trichloro-2,2,3-trifluoropropane, methylcyclohexane, 1-chloro-4-fluorobutane, 1-bromo-3-fluoropropane, 2,4,4-trimethyl-1-pentene, dioxane, 1-bromobutane, 3-pentanone, 1,1,2-trichloro-2-fluoroethane, 1,1-diethoxyethane, 2-pentanone, 2-methyl-2-butanol, 1-iodopropane, 2-methoxy-1-propanamine, 1,1,3-trichloro-1,2,2-trifluoropropane, 1,1,3-trichloro-2,2,3-trifluoropropane, trimethoxymethane, cis-1,3-dichloropropene, 2,2-dichlorobutane, n-pentylamine, 1,1-dichloro-2,2-difluoroethyl methyl ether, 2,2,4-trimethyl-2-pentene, 1,1,1,2-tetrachloro-2-fluoroethane, 1,3-dioxane, 3,3-dimethyl-2-butanone, piperidine, 1-bromo-2-chloroethane, 2-bromo-2-methylbutane, dipropylamine, 2,2,3,3-tetraflouro-1-propanol, 2-ethoxyethanamine, triethylfluorosilane, 1-methylcyclohexene, toluene, trans-1,3-dichloropropene, sec-butyl acetate, 2-fluorotoluene, 2,2-dimethyl-1-propanol, 1,1,1-trichloro-3-fluoropropane, n-methyl-1,2-ethanediamine, 2,2-diethoxypropane, 1,3,5-trioxane, 3,3,3-trichloro-1-propene, 1-chloro-3,3-dimethylbutane, pyridine, 2,3-dimethylhexane, 1,1,1,2-tetrachloro-3,3,3-trifluoropropane, n-methylmorpholine, 4-methyl-2-pentanone, 1,2-diaminoethane, isobutyl tert-butyl ether, 2-bromopentane, butyronitrile, 2,3-dichlorobutane, sec-butyl tert-butyl ether, 1-methoxy-2-propanol, 1,1,3,3-tetrachloro-1,2,2-trifluoropropane, 1,2-propanediamine, 2,6-dimethyl-5-heptenal, 1,1,1,3-tetrachloro-2,2,3-trifluoropropane, 1-bromo-3-methylbutane, 1,3-dichloro-trans-2-butene, 1,3-dichloropropane, 1-(dimethylamino)-2-propanol, tetrahydrothiophene, 3-methyl-3-pentanol, 1,2-dibromo-1-fluoroethane, 1,1-diethoxypropane, 1,2,2-trichloropropane, 1-chloro-2-methyl-2-propanol, 2-methoxyethanol, 1,2-dichlorobutane, 4,4,4-trifluorobutanol, 2-ethylbutylamine, diethyl carbonate, n-butyl acetate, 1-pentanethiol, 1,2,2,3-tetrachloro-3,3-difluoropropane, 2-chloro-1,1-dimethoxyethane, 2-hexanone, n-ethylethylenediamine, 3-fluoropropanol, 5-hexen-2-one, 2,3-dichloro-2-methylbutane, 1,1-diethoxy-n,n-dimethylmethanamine, 2-methylpyridine, 1-bromopentane, 2-methoxy-1-propanol, 1,2-dichloro-2-butene, 1-iodobutane, 1-ethoxy-2-propanol, hexanal, 4-methyl-2-pentanol, 1,2-dibromoethane, chlorobenzene, ethylcyclohexane, bromoacetic acid methyl ester, 1,1,2-trichloropropane, 1,2-octanediol, 4-methyl-2-hexanamine, hexylamine, 2-chloro-1-propanol, methoxycyclohexane, 2-(dimethylamino)ethanol, 1,3-dichlorobutane, cyclohexylamine, n-ethyl-2-dimethylaminoethylamine, ethoxyethanol, 3-hexanol, 2-hexanol, ethylbenzene, 2-methylpyrazine, 2-ethoxy-1-propanol, 1-methylpiperazine, n-ethylmorpholine, 1,4-dimethylbenzene, 1,3-dimethylbenzene, 1,3-propanediamine, di-n-butyl ether, 3,3,4,4,5,5,6,6-octafluoro-1-pentanol, valeronitrile, (methyleneamino)acetonitrile, 1,2-dibromopropane, 2-heptanamine, 1,2,3-trichloropropene, 1,2,3-trimethylcyclohexane, 2,3-dimethylbutanol, 1-ethoxyhexane, 1-chloro-3-bromopropane, 3-furfural, n,n-diethylethylenediamine, 2,6-dimethylpyridine, 1,1,3,3-tetrachloro-1-fluoropropane, 4-methyl-2-hexanone, 1,2-dimethylbenzene, 1,1,2,2,3-pentchloro-3,3-difluoropropane, 1-methoxy-2-acetoxypropane, 1,1,1-triethoxyethane, styrene, 4-methylpyridine, n,n'-diethyl-1,2-ethanediamine, 2,6-dimethylmorpholine, 2-ethyl-1-butanol, 1,2-dichloropentane, 2-methyl-1-pentanol, methyl hexanoate, 2-propoxyethanol, dimethylethanolamine or 1-propoxy-2-propanol.

Advantageously, said organic extracting agent may be chloroethane, ethylamine, bromofluoromethane, 1-bromo-1,2-difluoroethylene, acetaldehyde, 1-chloro-1,1-difluoropropane, 1,1,1-trifluoro-2-bromoethane, 1,1-dichloro-2,2,2-trifluoroethane, 1,2-dichloro-1,1,2-trifluoroethane, furan, methyl formate, isopropylamine, 2-methoxy-1-propene, diethyl ether, 1,2-epoxypropane, ethanethiol, 2-chloro-2-fluoropropane, ethoxyethene, 1-chloro-2,2-difluoroethane, dimethyl sulfide, 2-chloropropane, bromoethane, dimethoxymethane, 1-chloro-1,2,2-trifluoropropane, 2-amino-2-methylpropane, methyl cyclopropyl ether, 3-chloropropene, 3-chloro-1,1,1-trifluoropropane, 1,1,1-trichloro-2,2,2-trifluoroethane, 1,2-dichloro-1,2-difluoroethane, n-propylamine, 1,1,2-trichloro-1,2,2-trifluoroethane, ethanedial, 1-chloro-1,2,2,3-tetrafluoropropane, 2-chloro-2-methylpropane, 3-chloro-1,1,1,3-tetrafluoropropane, 2-chloro-1,1,1,3-tetrafluoropropane, 2-propanethiol, 1,2-dichloro-3,3,3-trifluoropropene, 2-ethoxypropane, 2,2-dichloro-1,1,1,3-tetrafluoropropane, 1-chloro-2,2-difluoropropane, methyl t-butyl ether, propanone, methyl acetate, ethyl 1,1,2,2-tetrafluoroethyl ether, 4-methoxy-2-methyl-2-butanethiol, 2-bromopropane, 1,1-dichloro-2,2-difluoroethane, 2,2-dichloro-1,1,3,3-tetrafluoropropane, difluorodiethylsilane, 2-butanamine, 2,3-dichloro-1,1,1,2-tetrafluoropropane, 1,1-dichloro-1,2,2,3-tetrafluoropropane, tert-butylthiol, isobutanal, 1,3-dichloro-1,1,2,2-tetrafluoropropane, 1,1,1-trichloro-2,2-difluoroethane, 1,2-dichloro-1,2,3,3-tetrafluoropropane, 1-propanethiol, 2-chlorobutane, isopropyl formate, diisopropyl ether, 1,3-dichloro-1,2,2,3-tetrafluoropropane, 1,2-dichloro-1,1,2,3-tetrafluoropropane, 2,3-dichloro-1,1,1,3-tetrafluoropropane, 1-bromopropane, 1,1-difluoro-1,2,2-trichloroethane, 1,1,2-trichloro-1,2-difluoroethane, methylglyoxal, 2-ethoxy-2-methylpropane, 2-bromo-2-methylpropane, 1-chloro-3-fluoropropane, 1,1,1-trifluoro-2-propanol, 2,3-dichloro-1,1,1-trifluoropropane, ethyl acetate, 1-butylamine, 1-chlorobutane, butanone, n-propyl formate, 2-ethoxybutane, 2-propanol, tert-butanol, 1,3-dichloro-1,1,2-trifluoropropane, 1-methoxy-2-methylbutane, 1,1-dichloro-2,2,3-trifluoropropane, cyclohexene, 2,2-dimethoxypropane, 1,3,3-trichloro-1,1,2,2-tetrafluoropropane, 2-chloro-2-methylbutane, 1-ethoxy-2-methylpropane, 2-butanethiol, 1,1,1-trichloro-2,2,3,3-tetrafluoropropane, 1,2-dimethoxyethane, 3-methyl-2-butanamine, 1,1,3-trichloro-1,2,2,3-tetrafluoropropane, 1,3-dichloro-1,2,2-trifluoropropane, diethoxymethane, 2-methyl-1-propanethiol, isopropyl acetate, 2-iodopropane, di-n-propyl ether, 3-pentylamine, n-methylbutylamine, 2-bromobutane, diethyl sulfide, 1-ethoxybutane, 1-fluorohexane, 1-methoxy-2-propanamine, 1,3-dichloro-1,2,3-trifluoropropane, 2-methoxyethanamine, 2-methylbutanal, propanol, tert-butyl acetate, propionitrile, 3-chloropentane, 2-allyloxyethanol, butanethiol, isoamyl chloride, 1-methoxypentane, ethyl propionate, 1,2-dimethoxypropane, isopropyl isobutyl ether, 1,1,1-trichloro-2,2,3-trifluoropropane, 1-chloro-4-fluorobutane, 1-bromo-3-fluoropropane, 2,4,4-trimethyl-1-pentene, dioxane, 1-bromobutane, 3-pentanone, 1,1-diethoxyethane, 2-pentanone, 2-methyl-2-butanol, 2-methoxy-1-propanamine, 1,1,3-trichloro-1,2,2-trifluoropropane, 1,1,3-trichloro-2,2,3-trifluoropropane, trimethoxymethane, n-pentylamine, 1,1-dichloro-2,2-difluoroethyl methyl ether, 2,2,4-trimethyl-2-pentene, 1,3-dioxane, 3,3-dimethyl-2-butanone, piperidine, 2-bromo-2-methylbutane, dipropylamine, 2,2,3,3-tetraflouro-1-propanol, 2-ethoxyethanamine, triethylfluorosilane, 1-methylcyclohexene, toluene, sec-butyl acetate, 2-fluorotoluene, 2,2-dimethyl-1-propanol, n-methyl-1,2-ethanediamine, 2,2-diethoxypropane, 1,3,5-trioxane, 1-chloro-3,3-dimethylbutane, pyridine, 1,1,1,2-tetrachloro-3,3,3-trifluoropropane, n-methylmorpholine, 4-methyl-2-pentanone, 1,2-diaminoethane, isobutyl tert-butyl ether, 2-bromopentane, butyronitrile, sec-butyl tert-butyl ether, 1-methoxy-2-propanol, 1,1,3,3-tetrachloro-1,2,2-trifluoropropane, 1,2-propanediamine, 2,6-dimethyl-5-heptenal, 1,1,1,3-tetrachloro-2,2,3-trifluoropropane, 1-bromo-3-methylbutane, 1-(dimethylamino)-2-propanol, tetrahydrothiophene, 3-methyl-3-pentanol, 1,1-diethoxypropane, 2-methoxyethanol, 4,4,4-trifluorobutanol, 2-ethylbutylamine, diethyl carbonate, n-butyl acetate, 1-pentanethiol, 2-chloro-1,1-dimethoxyethane, 2-hexanone, n-ethylethylenediamine, 5-hexen-2-one, 1,1-diethoxy-n,n-dimethylmethanamine, 2-methylpyridine, 1-bromopentane, 2-methoxy-1-propanol, 1-ethoxy-2-propanol, hexanal, 4-methyl-2-pentanol, 1,2-octanediol, 4-methyl-2-hexanamine, hexylamine, methoxycyclohexane, 2-(dimethylamino)ethanol, cyclohexylamine, n-ethyl-2-dimethylaminoethylamine, ethoxyethanol, 3-hexanol, 2-hexanol, ethylbenzene, 2-methylpyrazine, 2-ethoxy-1-propanol, 1-methylpiperazine, n-ethylmorpholine, 1,4-dimethylbenzene, 1,3-dimethylbenzene, 1,3-propanediamine, di-n-butyl ether, valeronitrile, (methyleneamino)acetonitrile, 2-heptanamine, 2,3-dimethylbutanol, 1-ethoxyhexane, 3-furfural, n,n-diethylethylenediamine, 2,6-dimethylpyridine, 4-methyl-2-hexanone, 1,2-dimethylbenzene, 1-methoxy-2-acetoxypropane, 1,1,1-triethoxyethane, styrene, 4-methylpyridine, n,n'-diethyl-1,2-ethanediamine, 2,6-dimethylmorpholine, 2-ethyl-1-butanol, 2-methyl-1-pentanol, methyl hexanoate, 2-propoxyethanol, dimethylethanolamine or 1-propoxy-2-propanol.

Preferably, said organic extracting agent may be acetaldehyde, methyl formate, 2-methoxy-1-propene, 1,2-epoxypropane, ethoxyethene, dimethoxymethane, 1-chloro-1,2,2-trifluoropropane, 3-chloro-1,1,1-trifluoropropane, ethanedial, 1-chloro-1,2,2,3-tetrafluoropropane, 3-chloro-1,1,1,3-tetrafluoropropane, 2-chloro-1,1,1,3-tetrafluoropropane, propanone, methyl acetate, 4-methoxy-2-methyl-2-butanethiol, difluorodiethylsilane, isobutanal, isopropyl formate, methylglyoxal, 2,3-dichloro-1,1,1-trifluoropropane, ethyl acetate, butanone, n-propyl formate, 1,3-dichloro-1,1,2-trifluoropropane, 1-methoxy-2-methyl-butane, 1,1-dichloro-2,2,3-trifluoropropane, 1,2-dimethoxyethane, 3-methyl-2-butanamine, 1,3-dichloro-1,2,2-trifluoropropane, diethoxymethane, isopropyl acetate, diethyl sulfide, 1-fluorohexane, 1-methoxy-2-propanamine, 1,3-dichloro-1,2,3-trifluoropropane, 2-methoxyethanamine, 2-methylbutanal, tert-butyl acetate, propionitrile, 2-allyloxyethanol, 1-methoxypentane, ethyl propionate, 1,2-dimethoxypropane, dioxane, 3-pentanone, 1,1-diethoxyethane, 2-pentanone, 2-methoxy-1-propanamine, trimethoxymethane, n-pentylamine, 1,3-dioxane, 3,3-dimethyl-2-butanone, 2-ethoxyethanamine, triethylfluorosilane, sec-butyl acetate, n-methyl-1,2-ethanediamine, 2,2-diethoxypropane, pyridine, n-methylmorpholine, 4-methyl-2-pentanone, 1,2-diaminoethane, isobutyl tert-butyl ether, butyronitrile, 1-methoxy-2-propanol, 1,2-propanediamine, 2,6-dimethyl-5-heptenal, 1-(dimethylamino)-2-propanol, 3-methyl-3-pentanol, 1,1-diethoxypropane, 2-ethylbutylamine, diethyl carbonate, n-butyl acetate, 2-hexanone, n-ethylethylenediamine, 5-hexen-2-one, 1,1-diethoxy-n,n-dimethylmethanamine, 2-methylpyridine, 2-methoxy-1-propanol, 1-ethoxy-2-propanol, hexanal, 4-methyl-2-hexanamine, hexylamine, methoxycyclohexane, 2-(dimethylamino)ethanol, cyclohexylamine, ethoxyethanol, 2-methylpyrazine, 2-ethoxy-1-propanol, 1-methylpiperazine, n-ethylmorpholine, 1,3-propanediamine, di-n-butyl ether, valeronitrile, 2-heptanamine, 1-ethoxyhexane, 2,6-dimethylpyridine, 4-methyl-2-hexanone, 1-methoxy-2-acetoxypropane, 1,1,1-triethoxyethane, 4-methylpyridine, 2,6-dimethylmorpholine, methyl hexanoate, 2-propoxyethanol or 1-propoxy-2-propanol.

In particular, said organic extracting agent may be methyl formate, -methoxy-1-propene, ethoxyethene, propanone, methyl acetate, isobutanal, isopropyl formate, ethyl acetate, butanone, n-propyl formate, 1,2-dimethoxyethane, isopropyl acetate, 1-methoxy-2-propanamine, 2-methoxyethanamine, 2-methylbutanal, tert-butyl acetate, ethyl propionate, dioxane, 3-pentanone, 2-pentanone, 2-methoxy-1-propanamine, trimethoxymethane, 1,3-dioxane, 3,3-dimethyl-2-butanone, 2-ethoxyethanamine, sec-butyl acetate, n-methyl-1,2-ethanediamine, 4-methyl-2-pentanone, 1,2-diaminoethane, butyronitrile, 1-methoxy-2-propanol, 1,2-propanediamine, 2,6-dimethyl-5-heptenal, 1-(dimethylamino)-2-propanol, diethyl carbonate, n-butyl acetate, 2-hexanone, n-ethylethylenediamine, 5-hexen-2-one, 2-methylpyridine, 2-methoxy-1-propanol, 1-ethoxy-2-propanol, hexanal, 2-(dimethylamino)ethanol, 2-methylpyrazine, 2-ethoxy-1-propanol, 1,3-propanediamine, valeronitrile, 2,6-dimethylpyridine, 4-methyl-2-hexanone, 1-methoxy-2-acetoxypropane, 4-methylpyridine, 2,6-dimethylmorpholine, methyl hexanoate, 2-propoxyethanol or 1-propoxy-2-propanol.

According to a particular embodiment, to allow optimum separation between 2,3,3,3-tetrafluoro-1-propene and a third composition comprising the organic extracting agent, chloromethane (40) and trans-1,3,3,3-tetrafluoro-1-propene (1234ze-E), the organic extract agent may be methyl formate, ethoxyethene, propanone, methyl acetate, isobutanal, isopropyl formate, ethyl acetate, butanone, isopropyl acetate, 2-methoxyethanamine, tert-butyl acetate, dioxane, 3-pentanone, 2-pentanone, 1,3-dioxane, 3,3-dimethyl-2-butanone, sec-butyl acetate, 4-methyl-2-pentanone, 1,2-diaminoethane, 1-methoxy-2-propanol, 1,2-propanediamine, diethyl carbonate, n-butyl acetate, 2-methoxy-1-propanol, 1-ethoxy-2-propanol or hexanal.

Thus, chloromethane and trans-1,3,3,3-tetrafluoro-1-propene may be separated from 2,3,3,3-tetrafluoro-1-propene.

The organic extracting agent to be used may be chosen as a function of the compounds present in said first composition. Thus, the organic extracting agent may be chosen as a function of the separation factor and of the absorption capacity established for a particular composition. Besides these two criteria, the choice of the organic extracting agent may be optionally based on other commercial or environmental criteria, for instance the cost of the organic extracting agent, its availability on the market, and its toxicity or flammability properties. Furthermore, according to a particular embodiment, in order to optimize the functioning of the distillation columns used in the steps b) and c) of the present process for purifying 2,3,3,3-tetrafluoro-1-propene, the boiling point of the organic extracting agent may be from 10° C. to 200° C., advantageously from 10° C. to 190° C., preferably from 10° C. to 180° C., in particular from 10° C. to 170° C., preferentially from 10° C. to 160° C. and more preferentially from 10° C. to 150° C.

According to a preferred embodiment, said organic extracting agent has a separation factor $S_{1,2}$ of greater than or equal to 1.1, said separation factor being calculated by the formula $S_{1,2}=(\gamma_{1,S}*P1)/(\gamma_{2,S}*P2)$ in which
$\gamma_{1,S}$ represents the activity coefficient of 2,3,3,3-tetrafluoro-1-propene in said organic extracting agent at infinite dilution;
P1 represents the saturating vapor pressure of 2,3,3,3-tetrafluoro-1-propene;
δ2,S represents the activity coefficient of chloromethane (40);
P2 represents the saturating vapor pressure of chloromethane (40).

Said separation factor, calculated for a 2,3,3,3-tetrafluoro-1-propene/chloromethane couple as defined above, may be greater than or equal to 1.2, advantageously greater than or equal to 1.4, more advantageously greater than or equal to 1.6, preferably greater than or equal to 1.8, more preferentially greater than or equal to 2.0.

Said organic extracting agent may have an absorption capacity $C_{2,S}$ of greater than or equal to 0.20, said absorption capacity being calculated by the formula $C_{2,S}=1/(\gamma_{2,S})$ in which γ2,S represents the activity coefficient of chloromethane (40) in said organic extracting agent at infinite dilution. Advantageously, the absorption capacity $C_{2,S}$, calculated for a 2,3,3,3-tetrafluoro-1-propene/chloromethane couple as defined above, is greater than or equal to 0.40, preferably greater than or equal to 0.60, more preferentially greater than or equal to 0.60, in particular greater than or equal to 1.0, more particularly greater than or equal to 1.1 and preferentially greater than or equal to 1.2.

Thus, for the 2,3,3,3-tetrafluoro-1-propene/chloromethane couple, said organic extracting agent may have a separation factor $S_{1,2}$ of greater than 1.1, advantageously greater than or equal to 1.2, preferably greater than or equal to 1.4, more preferentially greater than or equal to 1.6, in particular greater than or equal to 1.8 and more particularly greater than or equal to 2.0; and an absorption capacity $C_{2,S}$ of greater than or equal to 0.20, advantageously greater than or equal to 0.40, preferably greater than or equal to 0.60, more preferentially greater than or equal to 0.80, in particular greater than or equal to 1.0, more particularly greater than or equal to 1.1 and preferentially greater than or equal to 1.2.

According to a preferred embodiment, when the composition contains trans-1,3,3,3-tetrafluoro-1-propene (1234ze-E), said organic extracting agent may be chosen so as also to have a particular separation factor with respect to trans-1,3,3,3-tetrafluoro-1-propene (1234ze-E). For a 2,3,3,3-tetrafluoro-1-propene/trans-1,3,3,3-tetrafluoro-1-propene (1234ze-E) couple, the separation factor may be calculated by the formula $S_{1,2}=(\gamma_{1,S}*P1)/(\gamma_{2,S}*P2)$ in which
$\gamma_{1,S}$ represents the activity coefficient of 2,3,3,3-tetrafluoro-1-propene in said organic extracting agent at infinite dilution;
P1 represents the saturating vapor pressure of 2,3,3,3-tetrafluoro-1-propene;
$\gamma_{2,S}$ represents the activity coefficient of trans-1,3,3,3-tetrafluoro-1-propene (1234ze-E);
P2 represents the saturating vapor pressure of trans-1,3,3,3-tetrafluoro-1-propene (1234ze-E).

In this case, the separation factor $S_{1,2}$ may be greater than or equal to 1.1, advantageously greater than or equal to 1.2, preferably greater than or equal to 1.4, more preferentially greater than or equal to 1.6, in particular greater than or equal to 1.8, more particularly greater than or equal to 2.0.

Said organic extracting agent may also have an absorption capacity $C_{2,S}$ of greater than or equal to 0.20, said absorption capacity being calculated by the formula $C_{2,S}=1/(\gamma_{2,S})$ in which $\gamma_{2,S}$ represents the activity coefficient of trans-1,3,3,3-tetrafluoro-1-propene (1234ze-E) in said organic extracting agent at infinite dilution. Advantageously, the absorption capacity $C_{2,S}$ is greater than or equal to 0.40, preferably greater than or equal to 0.60, more preferentially greater than or equal to 0.60, in particular greater than or equal to 0.80, more particularly greater than or equal to 0.9 and preferentially greater than or equal to 1.0.

Said first composition may be an azeotropic or quasi-azeotropic composition comprising 2,3,3,3-tetrafluoro-1-propene, chloromethane (40) and optionally or not trans-1,3,3,3-tetrafluoro-1-propene (1234ze-E). Preferably, said first composition is an azeotropic or quasi-azeotropic composition comprising 2,3,3,3-tetrafluoro-1-propene, chloromethane (40) and trans-1,3,3,3-tetrafluoro-1-propene (1234ze-E). The content of each of the compounds in this particular composition is as expressed above with reference to the individual contents of each of the compounds.

Thus, the second composition may comprise 2,3,3,3-tetrafluoro-1-propene, chloromethane (40), said organic extracting agent, and optionally or not trans-1,3,3,3-tetrafluoro-1-propene (1234ze-E). Preferably, the second composition may comprise 2,3,3,3-tetrafluoro-1-propene, chloromethane (40), said organic extracting agent, and trans-1,3,3,3-tetrafluoro-1-propene (1234ze-E).

Thus, said organic extracting agent may have:
a separation factor $S_{1,2}$ of greater than or equal to 1.1, said separation factor being calculated by the formula $S_{1,2}=(\gamma_{1,S}*P1)/(\gamma_{2,S}*P2)$ in which $\gamma_{1,S}$ represents the activity coefficient of 2,3,3,3-tetrafluoro-1-propene in said organic extracting agent at infinite dilution, P1 represents the saturating vapor pressure of 2,3,3,3-tetrafluoro-1-propene, $\gamma_{2,S}$ represents the activity coefficient of chloromethane (40) in said organic extracting agent at infinite dilution and P2 represents the saturating vapor pressure of chloromethane (40); advantageously, said organic extracting agent may have a separation factor of greater than or equal to 1.2, preferably greater than or equal to 1.4, more preferentially greater than or equal to 1.6, in particular greater than or equal to 1.8 and more particularly greater than or equal to 2.0;

an absorption capacity $C_{2,S}$ of greater than or equal to 0.20, said absorption capacity being calculated by the formula $C_{2,S}=1/(\gamma_{2,S})$ in which $\gamma_{2,S}$ represents the activity coefficient of chloromethane (40) in said organic extracting agent at infinite dilution; advantageously, the absorption capacity $C_{2,S}$ may be greater than or equal to 0.40, preferably greater than or equal to 0.60, more preferentially greater than or equal to 0.80, in particular greater than or equal to 1.0;

a separation factor $S_{1,2}$ of greater than or equal to 1.1, said separation factor being calculated by the formula $S_{1,2}=(\gamma_{1,S}*P1)/(\gamma_{2,S}*P2)$ in which $\gamma_{1,S}$ represents the activity coefficient of 2,3,3,3-tetrafluoro-1-propene in said organic extracting agent at infinite dilution, P1 represents the saturating vapor pressure of 2,3,3,3-tetrafluoro-1-propene, $\gamma_{2,S}$ represents the activity coefficient of trans-1,3,3,3-tetrafluoro-1-propene (1234ze-E) in said organic extracting agent at infinite dilution and P2 represents the saturating vapor pressure of trans-1,3,3,3-tetrafluoro-1-propene (1234ze-E); advantageously, said organic extracting agent may have a separation factor of greater than or equal to 1.2, preferably greater than or equal to 1.4, more preferentially greater than or equal to 1.6, in particular greater than or equal to 1.8 and more particularly greater than or equal to 2.0; and an absorption capacity $C_{2,S}$ of greater than or equal to 0.20, said absorption capacity being calculated by the formula $C_{2,S}=1/(\gamma_{2,S})$ in which $\gamma_{2,S}$ represents the activity coefficient of trans-1,3,3,3-tetrafluoro-1-propene (1234ze-E) in said organic extracting agent at infinite dilution; advantageously, the absorption capacity $C_{2,S}$ is greater than or equal to 0.40, preferably greater than or equal to 0.60, more preferentially greater than or equal to 0.80, in particular greater than or equal to 1.0.

For example, said organic extracting agent may be chosen so as to have a separation factor of greater than or equal to 1.2 and so as to have an absorption capacity of greater than or equal to 0.4 for the two binary couples 2,3,3,3-tetrafluoro-1-propene/trans-1,3,3,3-tetrafluoro-1-propene (1234ze-E) and 2,3,3,3-tetrafluoro-1-propene/chloromethane (40). Thus, said organic extracting agent may be chosen from the group consisting of chloroethane, ethylamine, bromofluoromethane, 1-bromo-1,2-difluoroethylene, acetaldehyde, 1-chloro-1,1-difluoropropane, 1,1,1-trifluoro-2-bromoethane, 1,1-dichloro-2,2,2-trifluoroethane, 1,2-dichloro-1,1,2-trifluoroethane, furan, methyl formate, isopropylamine, 2-methoxy-1-propene, diethyl ether, 1,2-epoxypropane, ethanethiol, 2-chloro-2-fluoropropane, ethoxyethene, 1-chloro-2,2-difluoroethane, dimethyl sulfide, 2-chloropropane, bromoethane, dimethoxymethane, 1-chloro-1,2,2-trifluoropropane, 2-amino-2-methylpropane, methyl cyclopropyl ether, 3-chloropropene, 3-chloro-1,1,1-trifluoropropane, 1,1,1-trichloro-2,2,2-trifluoroethane, 1,2-dichloro-1,2-difluoroethane, n-propylamine, 1,1,2-trichloro-1,2,2-trifluoroethane, ethanedial, 1-chloro-1,2,2,3-tetrafluoropropane, 2-chloro-2-methylpropane, 3-chloro-1,1,1,3-tetrafluoropropane, 2-chloro-1,1,1,3-tetrafluoropropane, 2-propanethiol, 1,2-dichloro-3,3,3-trifluoropropane, 2-ethoxypropane, 2,2-dichloro-1,1,1,3-tetrafluoropropane, 1-chloro-2,2-difluoropropane, methyl t-butyl ether, propanone, methyl acetate, ethyl 1,1,2,2-tetrafluoroethyl ether, 4-methoxy-2-methyl-2-butanethiol, 2-bromopropane, 1,1-dichloro-2,2-difluoroethane, 2,2-dichloro-1,1,3,3-tetrafluoropropane, difluorodiethylsilane, 2-butanamine, 2,3-dichloro-1,1,1,2-tetrafluoropropane, 1,1-dichloro-1,2,2,3-tetrafluoropropane, tert-butylthiol, isobutanal, 1,3-dichloro-1,1,2,2-tetrafluoropropane, 1,1,1-trichloro-2,2-difluoroethane, 1,2-dichloro-1,2,3,3-tetrafluoropropane, 1-propanethiol, 2-chlorobutane, isopropyl formate, diisopropyl ether, 1,3-dichloro-1,2,2,3-tetrafluoropropane, 1,2-dichloro-1,1,2,3-tetrafluoropropane, 2,3-dichloro-1,1,1,3-tetrafluoropropane, 1-bromopropane, 1,1-difluoro-1,2,2-trichloroethane, 1,1,2-trichloro-1,2-difluoroethane, methylglyoxal, 2-ethoxy-2-methylpropane, 2-bromo-2-methylpropane, 1-chloro-3-fluoropropane, 1,1,1-trifluoro-2-propanol, 2,3-dichloro-1,1,1-trifluoropropane, ethyl acetate, 1-butylamine, 1-chlorobutane, butanone, n-propyl formate, 2-ethoxybutane, 2-propanol, tert-butanol, 1,3-dichloro-1,1,2-trifluoropropane, 1-methoxy-2-methylbutane, 1,1-dichloro-2,2,3-trifluoropropane, cyclohexene, 2,2-dimethoxypropane, 1,3,3-trichloro-1,1,2,2-tetrafluoropropane, 2-chloro-2-methylbutane, 1-ethoxy-2-methylpropane, 2-butanethiol, 1,1,1-trichloro-2,2,3,3-tetrafluoropropane, 1,2-dimethoxyethane, 3-methyl-2-butanamine, 1,1,3-trichloro-1,2,2,3-tetrafluoropropane, 1,3-dichloro-1,2,2-trifluoropropane, diethoxymethane, 2-methyl-1-propanethiol, isopropyl acetate, 2-iodopropane, di-n-propyl ether, 3-pentylamine, n-methylbutylamine, 2-bromobutane, diethyl sulfide, 1-ethoxybutane, 1-fluorohexane, 1-methoxy-2-propanamine, 1,3-dichloro-1,2,3-trifluoropropane, 2-methoxyethanamine, 2-methylbutanal, propanol, tert-butyl acetate, propionitrile, 3-chloropentane, 2-allyloxyethanol, butanethiol, isoamyl chloride, 1-methoxypentane, ethyl propionate, 1,2-dimethoxypropane, isopropyl isobutyl ether, 1,1,1-trichloro-2,2,3-trifluoropropane, 1-chloro-4-fluorobutane, 1-bromo-3-fluoropropane, 2,4,4-trimethyl-1-pentene, dioxane, 1-bromobutane, 3-pentanone, 1,1-diethoxyethane, 2-pentanone, 2-methyl-2-butanol, 2-methoxy-1-propanamine, 1,1,3-trichloro-1,2,2-trifluoropropane, 1,1,3-trichloro-2,2,3-trifluoropropane, trimethoxymethane, n-pentylamine, 1,1-dichloro-2,2-difluoroethyl methyl ether, 2,2,4-trimethyl-2-pentene, 1,3-dioxane, 3,3-dimethyl-2-butanone, piperidine, 2-bromo-2-methylbutane, dipropylamine, 2,2,3,3-tetraflouro-1-propanol, 2-ethoxyethanamine, triethylfluorosilane, 1-methylcyclohexene, toluene, sec-butyl acetate, 2-fluorotoluene, 2,2-dimethyl-1-propanol, n-methyl-1,2-ethanediamine, 2,2-diethoxypropane, 1,3,5-trioxane, 1-chloro-3,3-dimethylbutane, pyridine, 1,1,1,2-tetrachloro-3,3,3-trifluoropropane, n-methylmorpholine, 4-methyl-2-pentanone, 1,2-diaminoethane, isobutyl tert-butyl ether, 2-bromopentane, butyronitrile, sec-butyl tert-butyl ether, 1-methoxy-2-propanol, 1,1,3,3-tetrachloro-1,2,2-trifluoropropane, 1,2-propanediamine, 2,6-dimethyl-5-heptenal, 1,1,1,3-tetrachloro-2,2,3-trifluoropropane, 1-bromo-3-methylbutane, 1-(dimethylamino)-2-propanol, tetrahydrothiophene, 3-methyl-3-pentanol, 1,1-diethoxypropane, 2-methoxyethanol, 4,4,4-trifluorobutanol, 2-ethylbutylamine, diethyl carbonate, n-butyl acetate, 1-pentanethiol, 2-chloro-1,1-dimethoxyethane, 2-hexanone, n-ethylethylenediamine, 5-hexen-2-one, 1,1-diethoxy-n,n-dimethylmethanamine, 2-methylpyridine, 1-bromopentane, 2-methoxy-1-propanol, 1-ethoxy-2-propanol, hexanal, 4-methyl-2-pentanol, 1,2-octanediol, 4-methyl-2-hexanamine, hexylamine, methoxycyclohexane, 2-(dimethylamino)ethanol, cyclohexylamine, n-ethyl-2-dimethylaminoethylamine, ethoxyethanol, 3-hexanol, 2-hexanol, ethylbenzene, 2-methylpyrazine, 2-ethoxy-1-propanol, 1-methylpiperazine, n-ethylmorpholine, 1,4-dimethylbenzene, 1,3-dimethylbenzene, 1,3-propanediamine, di-n-butyl ether, valeronitrile, (methyleneamino)acetonitrile, 2-heptanamine, 2,3-dimethylbutanol, 1-ethoxyhexane, 3-furfural, n,n-diethylethylenediamine, 2,6-dimethylpyridine, 4-methyl-2-hexanone, 1,2-dimethylbenzene, 1-methoxy-2-acetoxypropane, 1,1,1-triethoxyethane, styrene, 4-methylpyridine, n,n'-diethyl-1,2-ethanediamine, 2,6-dimethylmorpholine, 2-ethyl-1-butanol, 2-methyl-1-pentanol, methyl hexanoate, 2-propoxyethanol, dimethylethanolamine and 1-propoxy-2-propanol.

For example, said organic extracting agent may be chosen so as to have a separation factor of greater than or equal to 1.4 and so as to have an absorption capacity of greater than or equal to 0.6 for the two binary couples 2,3,3,3-tetrafluoro-1-propene/trans-1,3,3,3-tetrafluoro-1-propene (1234ze-E) and 2,3,3,3-tetrafluoro-1-propene/chloromethane (40). Thus, said organic extracting agent may be chosen from the group consisting of acetaldehyde, methyl formate, 2-methoxy-1-propene, 1,2-epoxypropane, ethoxyethene, dimethoxymethane, 1-chloro-1,2,2-trifluoropropane, 3-chloro-1,1,1-trifluoropropane, ethanedial, 1-chloro-1,2,2,3-tetrafluoropropane, 3-chloro-1,1,1,3-tetrafluoropropane, 2-chloro-1,1,1,3-tetrafluoropropane, propanone, methyl acetate, 4-methoxy-2-methyl-2-butanethiol, difluorodiethylsilane, isobutanal, isopropyl formate, methylglyoxal, 2,3-dichloro-1,1,1-trifluoropropane, ethyl acetate, butanone, n-propyl formate, 1,3-dichloro-1,1,2-trifluoropropane, 1-methoxy-2-methylbutane, 1,1-dichloro-2,2,3-trifluoropropane, 1,2-dimethoxyethane, 3-methyl-2-butanamine, 1,3-dichloro-1,2,2-trifluoropropane, diethoxymethane, isopropyl acetate, diethyl sulfide, 1-fluorohexane, 1-methoxy-2-propanamine, 1,3-dichloro-1,2,3-trifluoropropane, 2-methoxyethanamine, 2-methylbutanal, tert-butyl acetate, propionitrile, 2-allyloxyethanol, 1-methoxypentane, ethyl propionate, 1,2-dimethoxypropane, dioxane, 3-pentanone, 1,1-diethoxyethane, 2-pentanone, 2-methoxy-1-propanamine, trimethoxymethane, n-pentylamine, 1,3-dioxane, 3,3-dimethyl-2-butanone, 2-ethoxyethanamine, triethylfluorosilane, sec-butyl acetate, n-methyl-1,2-ethanediamine, 2,2-diethoxypropane, pyridine, n-methylmorpholine, 4-methyl-2-pentanone, 1,2-diaminoethane, isobutyl tert-butyl ether, butyronitrile, 1-methoxy-2-propanol, 1,2-propanediamine, 2,6-dimethyl-5-heptenal, 1-(dimethylamino)-2-propanol, 3-methyl-3-pentanol, 1,1-diethoxypropane, 2-ethylbutylamine, diethyl carbonate, n-butyl acetate, 2-hexanone, n-ethylethylenediamine, 5-hexen-2-one, 1,1-diethoxy-n,n-dimethylmethanamine, 2-methylpyridine, 2-methoxy-1-propanol, 1-ethoxy-2-propanol, hexanal, 4-methyl-2-hexanamine, hexylamine, methoxycyclohexane, 2-(dimethylamino)ethanol, cyclohexylamine, ethoxyethanol, 2-methylpyrazine, 2-ethoxy-1-propanol, 1-methylpiperazine, n-ethylmorpholine, 1,3-propanediamine, di-n-butyl ether, valeronitrile, 2-heptanamine, 1-ethoxyhexane, 2,6-dimethylpyridine, 4-methyl-2-hexanone, 1-methoxy-2-acetoxypropane, 1,1,1-triethoxyethane, 4-methylpyridine, 2,6-dimethylmorpholine, methyl hexanoate, 2-propoxyethanol and 1-propoxy-2-propanol.

For example, said organic extracting agent may be chosen so as to have a separation factor of greater than or equal to 1.6 and so as to have an absorption capacity of greater than or equal to 0.8 for the two binary couples 2,3,3,3-tetrafluoro-1-propene/trans-1,3,3,3-tetrafluoro-1-propene (1234ze-E) and 2,3,3,3-tetrafluoro-1-propene/chloromethane (40). Thus, said organic extracting agent may be chosen from the group consisting of methyl formate, -methoxy-1-propene, ethoxyethene, propanone, methyl acetate, isobutanal, isopropyl formate, ethyl acetate, butanone, n-propyl formate, 1,2-dimethoxyethane, isopropyl acetate, 1-methoxy-2-propanamine, 2-methoxyethanamine, 2-methylbutanal, tert-butyl acetate, ethyl propionate, dioxane, 3-pentanone, 2-pentanone, 2-methoxy-1-propanamine, trimethoxymethane, 1,3-dioxane, 3,3-dimethyl-2-butanone, 2-ethoxyethanamine, sec-butyl acetate, n-methyl-1,2-ethanediamine, 4-methyl-2-pentanone, 1,2-diaminoethane, butyronitrile, 1-methoxy-2-propanol, 1,2-propanediamine, 2,6-dimethyl-5-heptenal, 1-(dimethylamino)-2-propanol, diethyl carbonate, n-butyl acetate, 2-hexanone, n-ethylethylenediamine, 5-hexen-2-one, 2-methylpyridine, 2-methoxy-1-propanol, 1-ethoxy-2-propanol, hexanal, 2-(dimethylamino)ethanol, 2-methylpyrazine, 2-ethoxy-1-propanol, 1,3-propanediamine, valeronitrile, 2,6-dimethylpyridine, 4-methyl-2-hexanone, 1-methoxy-2-acetoxypropane, 4-methylpyridine, 2,6-dimethylmorpholine, methyl hexanoate, 2-propoxyethanol and 1-propoxy-2-propanol.

Preferably, said organic extracting agent may be methyl formate, ethoxyethene, propanone, methyl acetate, isobutanal, isopropyl formate, ethyl acetate, butanone, isopropyl acetate, 2-methoxyethanamine, tert-butyl acetate, dioxane, 3-pentanone, 2-pentanone, 1,3-dioxane, 3,3-dimethyl-2-butanone, sec-butyl acetate, 4-methyl-2-pentanone, 1,2-diaminoethane, 1-methoxy-2-propanol, 1,2-propanediamine, diethyl carbonate, n-butyl acetate, 2-methoxy-1-propanol, 1-ethoxy-2-propanol or hexanal. In particular, said organic extracting agent may be methyl formate, propanone, butanone, isopropyl acetate, 2-methoxyethanamine, tert-butyl acetate, dioxane, 1,3-dioxane, sec-butyl acetate, 1,2-diaminoethane, 1-methoxy-2-propanol, 1,2-propanediamine, n-butyl acetate, 2-methoxy-1-propanol, 1-ethoxy-2-propanol or hexanal, more particularly methyl formate, isopropyl acetate, 2-methoxyethanamine, tert-butyl acetate, dioxane, 1,3-dioxane, sec-butyl acetate, 1,2-diaminoethane, 1-methoxy-2-propanol, 1,2-propanediamine, n-butyl acetate, 2-methoxy-1-propanol, 1-ethoxy-2-propanol or hexanal.

According to a particular embodiment, the stream comprising 2,3,3,3-tetrafluoropropene separated out in step b) of the present process is subsequently purified or liquefied and stored. According to this embodiment, traces of organic extracting agent may be present in the stream comprising 2,3,3,3-tetrafluoropropene. The traces of organic extracting agent in said stream are less than 10 ppm, preferably less than 1 ppm, in particular less than 500 ppb and more particularly less than 100 ppb.

The present process thus makes it possible to purify 2,3,3,3-tetrafluoro-1-propene. Advantageously, the content of chloromethane (40) and/or trans-1,3,3,3-tetrafluoro-1-propene (1234ze-E) in the stream comprising 2,3,3,3-tetrafluoro-1-propene, obtained in step b) of the present purification process, is less than the content of that or those in said first composition. Advantageously, the content of chloromethane (40) and trans-1,3,3,3-tetrafluoro-1-propene (1234ze-E) in the stream comprising 2,3,3,3-tetrafluoro-1-propene, obtained in step b) of the present purification process, is less than the respective content thereof in said first composition. For example, the content of chloromethane (40) and/or trans-1,3,3,3-tetrafluoro-1-propene (1234ze-E) may be reduced by 50%, advantageously by 75%, preferably by 90%, in particular by 95% and more particularly by 98%. Preferably, the stream comprising 2,3,3,3-tetrafluoro-1-propene obtained in step b) of the present purification process may be free of chloromethane (40) and/or trans-1,3,3,3-tetrafluoro-1-propene (1234ze-E) when this or these compounds are present in said first composition. In particular, the stream comprising 2,3,3,3-tetrafluoro-1-propene obtained in step b) of the present purification process may be free of chloromethane (40) and the content of trans-1,3,3,3-tetrafluoro-1-propene (1234ze-E) may be reduced by 50%, advantageously 75%, preferably 90%, in particular 95% and more particularly 98%. The contents are expressed as weight percentages.

According to a preferred embodiment, said first composition used in step a) of the present process may be purified before being used. Specifically, if said first composition comprises impurities with a boiling point below the boiling point of 2,3,3,3-tetrafluoro-1-propene and optionally heavy impurities, the process may comprise, prior to step a), the following steps:

i') use or provision of a composition comprising 2,3,3,3-tetrafluoro-1-propene, impurities with a boiling point below the boiling point of 2,3,3,3-tetrafluoro-1-propene, and chloromethane (40) and optionally or not trans-1,3,3,3-tetrafluoro-1-propene (1234ze-E), and optionally or not heavy impurities;

ii') distillation of said composition from step i) to remove, at the top of the column, impurities with a boiling point below the boiling point of 2,3,3,3-tetrafluoro-1-propene and to form a first stream comprising 2,3,3,3-tetrafluoro-1-propene, chloromethane (40) and optionally or not trans-1,3,3,3-tetrafluoro-1-propene (1234ze-E), and optionally or not heavy impurities, recovered at the bottom of the distillation column;

iii') optionally or not, distillation of said first stream recovered at the bottom of the distillation column in step ii') to recover, at the top of the column, a second stream comprising 2,3,3,3-tetrafluoro-1-propene, chloromethane (40) and optionally or not trans-1,3,3,3-tetrafluoro-1-propene (1234ze-E); and, at the bottom of the distillation column, a stream comprising the heavy impurities; said at first stream recovered in step ii') or said second stream recovered in step iii') corresponds to said first composition used in step a).

Preferably, the present process may comprise, before step a), the following steps:

i') use or provision of a composition comprising 2,3,3,3-tetrafluoro-1-propene, impurities with a boiling point below the boiling point of 2,3,3,3-tetrafluoro-1-propene, and chloromethane (40) and trans-1,3,3,3-tetrafluoro-1-propene (1234ze-E), and optionally or not heavy impurities;

ii') distillation of said composition from step i) to remove, at the top of the column, impurities with a boiling point below the boiling point of 2,3,3,3-tetrafluoro-1-propene and to form a first stream comprising 2,3,3,3-tetrafluoro-1-propene, chloromethane (40) and trans-1,3,3,3-tetrafluoro-1-propene (1234ze-E), and optionally or not heavy impurities, recovered at the bottom of the distillation column;

iii') optionally or not, distillation of said first stream recovered at the bottom of the distillation column in step ii') to recover, at the top of the column, a second stream comprising 2,3,3,3-tetrafluoro-1-propene, chloromethane (40) and trans-1,3,3,3-tetrafluoro-1-propene (1234ze-E); and, at the bottom of the distillation column, a stream comprising the heavy impurities;

said at first stream recovered in step ii') or said second stream recovered in step iii') corresponds to said first composition used in step a).

Said impurities with a boiling point below the boiling point of 2,3,3,3-tetrafluoro-1-propene may be trifluoromethane (F23), monofluoromethane (F41), difluoromethane (F32), pentafluoroethane (F125), 1,1,1-trifluoroethane (F143a), trifluoropropyne or 1-chloro-pentafluoroethane (F115). The heavy impurities may contain, for example, 1,1,1,3,3,3-hexafluoropropane (236fa), 1,1,1,2,3,3-hexafluoropropane (236ea), 1,1,1,2,3,3,3-heptafluoropropane (227ca), cis-1,3,3,3-tetrafluoro-1-propene (1234ze-Z), and dimers or trimers derived from one of the compounds present in the composition or the stream under consideration, for example C4 or C5 hydrocarbons such as hexafluorobutene (1336), heptafluorobutene (1327), octafluorobutane (338), nonafluoropentene (1429) or heptafluoropentene (1447).

According to a second aspect, the present invention provides a process for producing 2,3,3,3-tetrafluoro-1-propene. In addition, this process may include the purification thereof. Thus, the present invention provides a process for producing 2,3,3,3-tetrafluoro-1-propene, comprising the steps of:

A) fluorination in the presence of a catalyst of a compound of formula $CX(Y)_2$—$CX(Y)_m$—$CH_mXY$ (I) in which X and Y independently represent H, F or Cl and m=0 or 1; and/or fluorination in the presence of a catalyst of a compound of formula $(CX_nY_{3-n})CH_pX_{1-p}CH_mX_{2-m}$ (II) in which X is, independently of each other, Cl, F, I or Br; Y is, independently of each other, H, Cl, F, I or Br; n is 1, 2 or 3; and m is 0, 1 or 2; and p is 0 or 1;

B) recovery of a stream comprising 2,3,3,3-tetrafluoro-1-propene, chloromethane (40) and optionally or not trans-1,3,3,3-tetrafluoro-1-propene (1234ze-E);

C) implementation of the process for purifying 2,3,3,3-tetrafluoro-1-propene according to the present invention using the stream recovered in step B).

Thus, the process for producing 2,3,3,3-tetrafluoro-1-propene, comprising the steps of:

A) fluorination in the presence of a catalyst of a compound of formula $CX(Y)_2$—$CX(Y)_m$—$CH_mXY$ (I) in which X and Y independently represent H, F or Cl and m=0 or 1; and/or fluorination in the presence of a catalyst of a compound of formula $(CX_nY_{3-n})CH_pX_{1-p}CH_mX_{2-m}$ (II) in which X is, independently of each other, Cl, F, I or Br; Y is, independently of each other, H, Cl, F, I or Br; n is 1, 2 or 3; and m is 0, 1 or 2; and p is 0 or 1;

B) recovery of a stream comprising 2,3,3,3-tetrafluoro-1-propene, chloromethane (40) and trans-1,3,3,3-tetrafluoro-1-propene (1234ze-E);

C) implementation of the process for purifying 2,3,3,3-tetrafluoro-1-propene according to the present invention using the stream recovered in step B).

According to a preferred embodiment, the process for producing 2,3,3,3-tetrafluoro-1-propene comprising the steps of:

A) fluorination in the presence of a catalyst of a compound of formula $CX(Y)_2$—$CX(Y)_m$—$CH_mXY$ (I) in which X and Y independently represent H, F or Cl and m=0 or 1; and/or fluorination in the presence of a catalyst of a compound of formula $(CX_nY_{3-n})CH_pX_{1-p}CH_mX_{2-m}$ (II) in which X is, independently of each other, Cl, F, I or Br; Y is, independently of each other, H, Cl, F, I or Br; n is 1, 2 or 3; and m is 0, 1 or 2; and p is 0 or 1;

B) recovery of a stream comprising 2,3,3,3-tetrafluoro-1-propene, chloromethane (40) and optionally or not trans-1,3,3,3-tetrafluoro-1-propene (1234ze-E);

C) implementation of the process for purifying 2,3,3,3-tetrafluoro-1-propene using the stream recovered in step B) and comprising the steps of:

a) placing said first composition in contact with at least one organic extracting agent to form a second composition;
b) extractive distillation of said second composition to form:
   i) a third composition comprising said organic extracting agent and chloromethane (40) and optionally or not trans-1,3,3,3-tetrafluoro-1-propene (1234ze-E); and
   ii) a stream comprising 2,3,3,3-tetrafluoro-1-propene;
c) recovery and separation of said third composition to form a stream comprising said organic extracting agent and a stream comprising chloromethane (40) and optionally or not trans-1,3,3,3-tetrafluoro-1-propene (1234ze-E); preferably, the stream comprising said organic extracting agent is recycled into step a).

Preferably, the process for producing 2,3,3,3-tetrafluoro-1-propene comprising the steps of:
A) fluorination in the presence of a catalyst of a compound of formula $CX(Y)_2$—$CX(Y)_m$—$CH_mXY$ (I) in which X and Y independently represent H, F or Cl and m=0 or 1; and/or fluorination in the presence of a catalyst of a compound of formula $(CX_nY_{3-n})CH_pX_{1-p}$$CH_mX_{2-m}$ (II) in which X is, independently of each other, Cl, F, I or Br; Y is, independently of each other, H, Cl, F, I or Br; n is 1, 2 or 3; and m is 0, 1 or 2; and p is 0 or 1;
B) recovery of a stream comprising 2,3,3,3-tetrafluoro-1-propene, chloromethane (40) and trans-1,3,3,3-tetrafluoro-1-propene (1234ze-E);
C) implementation of the process for purifying 2,3,3,3-tetrafluoro-1-propene using the stream recovered in step B) and comprising the steps of:
   a) placing said first composition in contact with at least one organic extracting agent to form a second composition;
   b) extractive distillation of said second composition to form:
      iii) a third composition comprising said organic extracting agent and chloromethane (40) and trans-1,3,3,3-tetrafluoro-1-propene (1234ze-E); and
      iv) a stream comprising 2,3,3,3-tetrafluoro-1-propene;
   c) recovery and separation of said third composition to form a stream comprising said organic extracting agent and a stream comprising chloromethane (40) and trans-1,3,3,3-tetrafluoro-1-propene (1234ze-E); preferably, the stream comprising said organic extracting agent is recycled into step a).

According to a particular embodiment, the stream recovered in step B) of the process for producing 2,3,3,3-tetrafluoro-1-propene may comprise hydrofluoric acid. In this case, prior to step C), the stream recovered in step B) may undergo a preliminary distillation B1') to remove HF at the bottom of the distillation column. A stream comprising 2,3,3,3-tetrafluoro-1-propene, chloromethane (40) and optionally or not trans-1,3,3,3-tetrafluoro-1-propene (1234ze-E), is recovered at the top of the distillation column; preferably, a stream comprising 2,3,3,3-tetrafluoro-1-propene, chloromethane (40) and trans-1,3,3,3-tetrafluoro-1-propene (1234ze-E). The latter stream recovered at the top of the distillation column is then subjected to step C) of the process for producing 2,3,3,3-tetrafluoro-1-propene.

According to a particular embodiment, the stream recovered in step B) of the process for producing 2,3,3,3-tetrafluoro-1-propene may comprise impurities with a boiling point below the boiling point of 2,3,3,3-tetrafluoro-1-propene. In this case, prior to step C), the stream recovered in step B) may undergo a preliminary distillation B2') optionally subsequent to step B1'), to remove, at the top of the distillation column, said impurities with a boiling point below the boiling point of 2,3,3,3-tetrafluoro-1-propene and to form a first stream comprising 2,3,3,3-tetrafluoro-1-propene, chloromethane (40) and optionally or not trans-1,3,3,3-tetrafluoro-1-propene (1234ze-E) recovered at the bottom of the distillation column, preferably to form a first stream comprising 2,3,3,3-tetrafluoro-1-propene, chloromethane (40) and trans-1,3,3,3-tetrafluoro-1-propene (1234ze-E). The latter stream recovered at the bottom of the distillation column may then be subjected to step C) of the process for producing 2,3,3,3-tetrafluoro-1-propene.

According to a particular embodiment, the stream recovered in step B) of the process for producing 2,3,3,3-tetrafluoro-1-propene may comprise heavy impurities. In this case, prior to step C), the stream recovered in step B) may undergo a preliminary distillation B3') optionally subsequent to step B1') and/or B2'), to remove, at the bottom of the distillation column, said heavy impurities; and to form a first stream comprising 2,3,3,3-tetrafluoro-1-propene, chloromethane (40) and optionally or not trans-1,3,3,3-tetrafluoro-1-propene (1234ze-E) recovered at the top of the distillation column. Preferably, the first stream comprises 2,3,3,3-tetrafluoro-1-propene, chloromethane (40) and trans-1,3,3,3-tetrafluoro-1-propene (1234ze-E). The latter stream recovered at the top of the distillation column is then subjected to step C) of the process for producing 2,3,3,3-tetrafluoro-1-propene.

According to a particular embodiment, the stream recovered in step B) of the process for producing 2,3,3,3-tetrafluoro-1-propene may also comprise HCl. The hydrochloric acid may be recovered by distillation before or after step B1', independently of the other steps of the process.

More particularly, step A) is performed using 1,1,2,3-tetrachloropropene, 2,3,3,3,-tetrachloropropene, 1,1,3,3-tetrachloropropene, 1,3,3,3-tetrachloropropene, 1,1,1,2,3-pentachloropropane, 1,1,1,3,3-pentachloropropane, 1,1,2,2,3-pentachloropropane, 1,2-dichloro-3,3,3-trifluoropropane, 2-chloro-2,3,3,3-tetrafluoropropane, 1,1,1,2,2-pentafluoropropane, 1-chloro-1,3,3,3-tetrafluoropropane and 1,1,1,3,3-pentafluoropropane, preferably using 1,1,1,2,3-pentachloropropane, 1,1,2,3,tetrachloropropene, 1,1,1,2,2-pentafluoropropane and/or 2-chloro-3,3,3-trifluoro-1-propene; in particular using 1,1,1,2,3-pentachloropropane (240db).

FIG. 1a schematically represents a simplified scheme of a device for performing a process for purifying 2,3,3,3-tetrafluoro-1-propene according to a particular embodiment of the invention. The mixture derived from the fluorination reaction, in the presence of a catalyst, a compound of formula $CX(Y)_2$—$CX(Y)_m$—$CH_mXY$ (I) and/or catalytic fluorination, in the presence of a catalyst, a compound of formula $(CX_nY_{3-n})CH_pX_{1-p}$=$CH_mX_{2-m}$ (II) is obtained in 1. In this particular embodiment, the mixture comprises 2,3,3,3-tetrafluoro-1-propene, chloromethane and trans-1,3,3,3-tetrafluoro-1-propene (1234ze-E), impurities with a boiling point below the boiling point of 2,3,3,3-tetrafluoro-1-propene and heavy impurities. The mixture is transferred into a distillation column 2 via pipe 3. The impurities with a boiling point below the boiling point of 2,3,3,3-tetrafluoro-1-propene are recovered at the top of distillation column 2 and conveyed via pipe 5 to an incinerator or a purification device 15. The residue obtained at the bottom of the distillation column and comprising the other constituents of the mixture is conveyed to a second distillation column 6 via pipe 4. The distillation performed in 6 is directed toward separating the heavy impurities from the other constituents of the mixture. The distillation operating conditions are thus suitable for this purpose. The heavy impurities are recovered at the bottom of the distillation column 8 and the other constituents are recovered at the top of the distillation column and conveyed to the extractive distillation column 9 via pipe 7. The extractive distillation performed in 9 is directed toward separating 2,3,3,3-tetrafluoro-1-propene from the other constituents of the mixture mentioned above. The extractive distillation device 9 is fed with the organic extracting agent 17 chosen according to the method described in the present patent application. 2,3,3,3-Tetrafluoro-1-propene is recovered at the top of the extractive distillation column 9 and stored or purified in 10 via pipe 11. The mixture recovered at the bottom of the extractive distillation device 9 especially comprises the organic extracting agent 17, chloromethane (40) and trans-1,3,3,3-tetrafluoro-1-propene (1234ze-E). The mixture recovered at the bottom of the extractive distillation device 9 is conveyed via pipe at 12 to a distillation device 13 which is directed toward separating the organic extracting agent from the other compounds present. The organic extracting agent is recovered at the bottom of the distillation device 13 and recycled via pipe 16 to the extractive distillation device 9. The compounds recovered at the top of the distillation device 13 are conveyed via pipe 14 to pipe 5 to be incinerated or purified in 15.

Figure 1B:
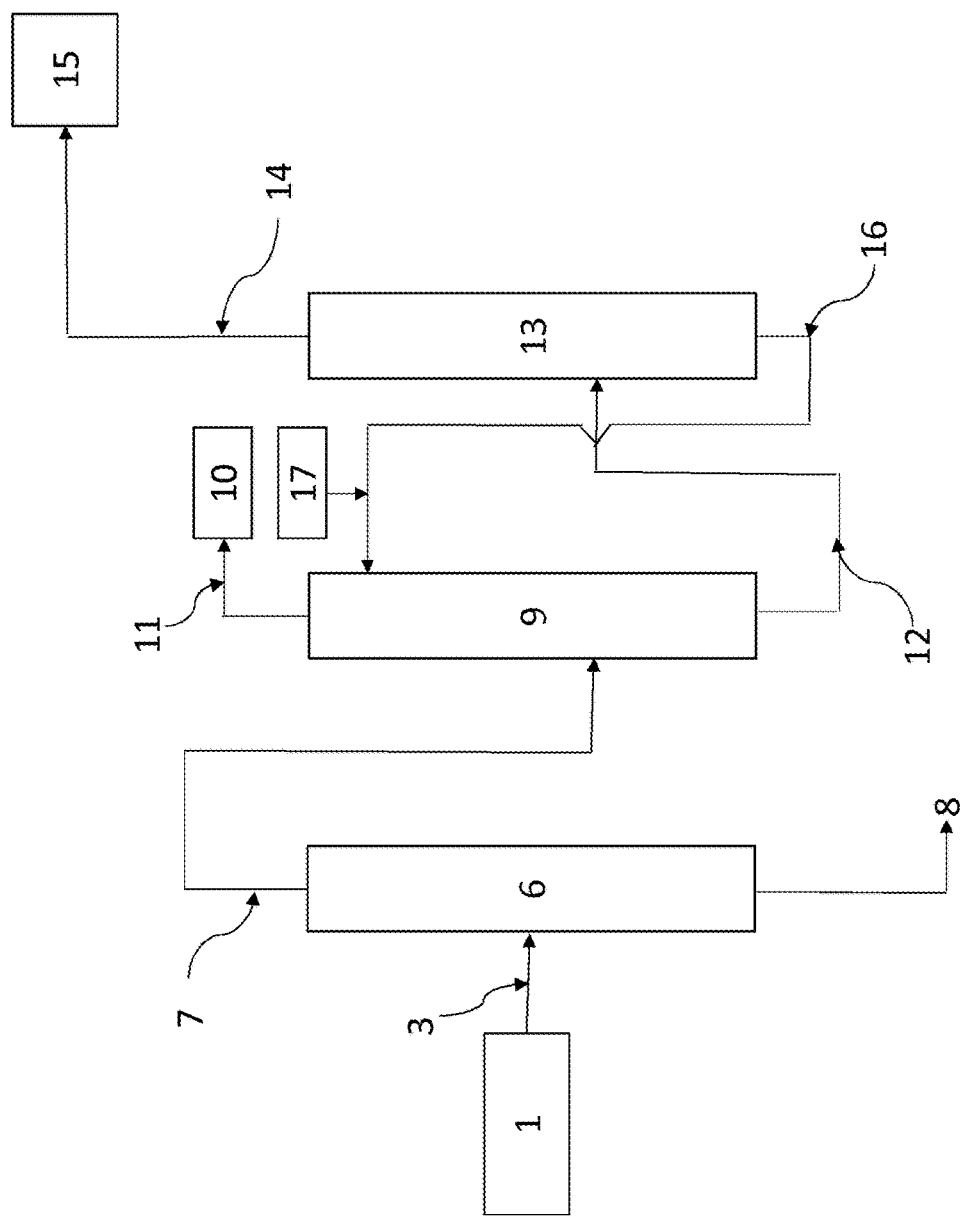
Figure 1C:
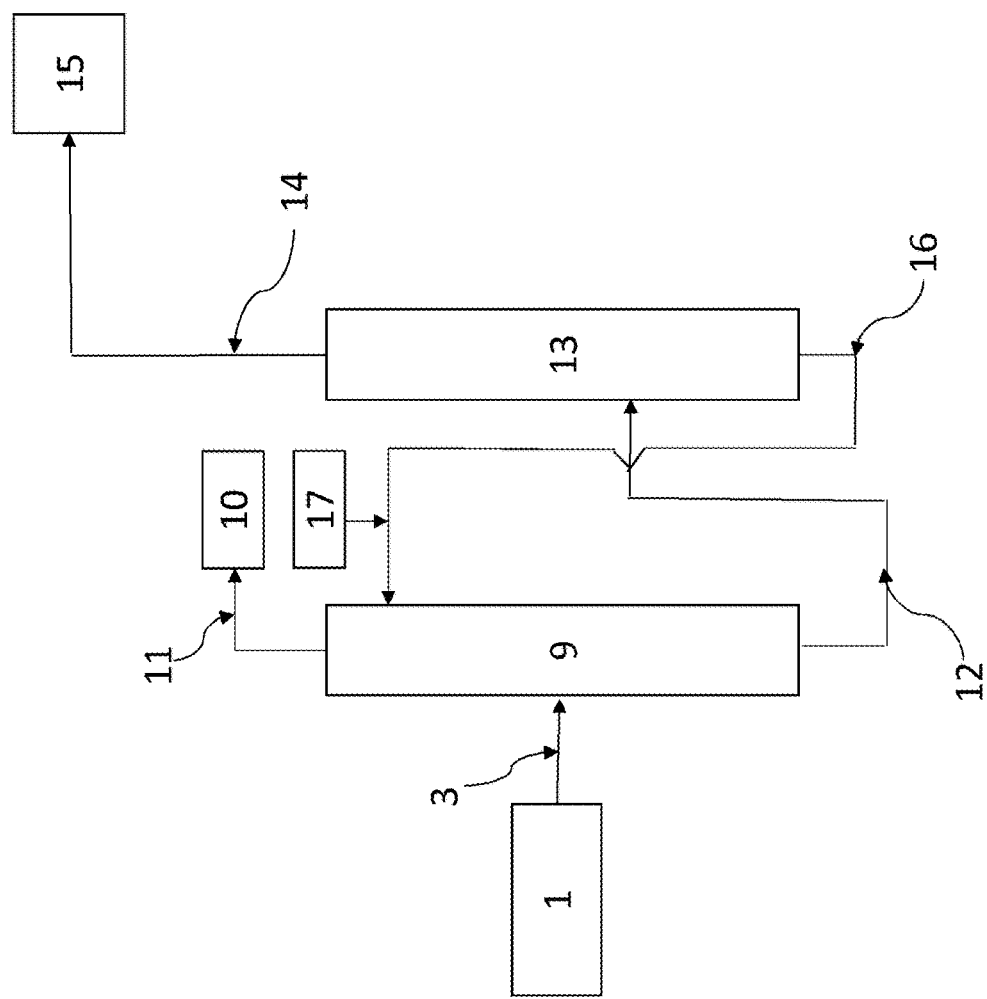

The mixture provided in 1 may be free of impurities with a boiling point below that of 2,3,3,3-tetrafluoro-1-propene. In this case, as illustrated in FIG. 1*b*, the mixture 1 is conveyed via pipe 3 to the distillation column 6 to be processed as explained above in relation with FIG. 1*a*. In another particular embodiment illustrated in FIG. 1*c*, the mixture 1 may comprise 2,3,3,3-tetrafluoro-1-propene, chloromethane and trans-1,3,3,3-tetrafluoro-1-propene (1234ze-E). In this case, the mixture is conveyed directly to the extractive distillation column 9 to be processed therein as explained above in relation with FIG. 1*a*.

Figure 2:
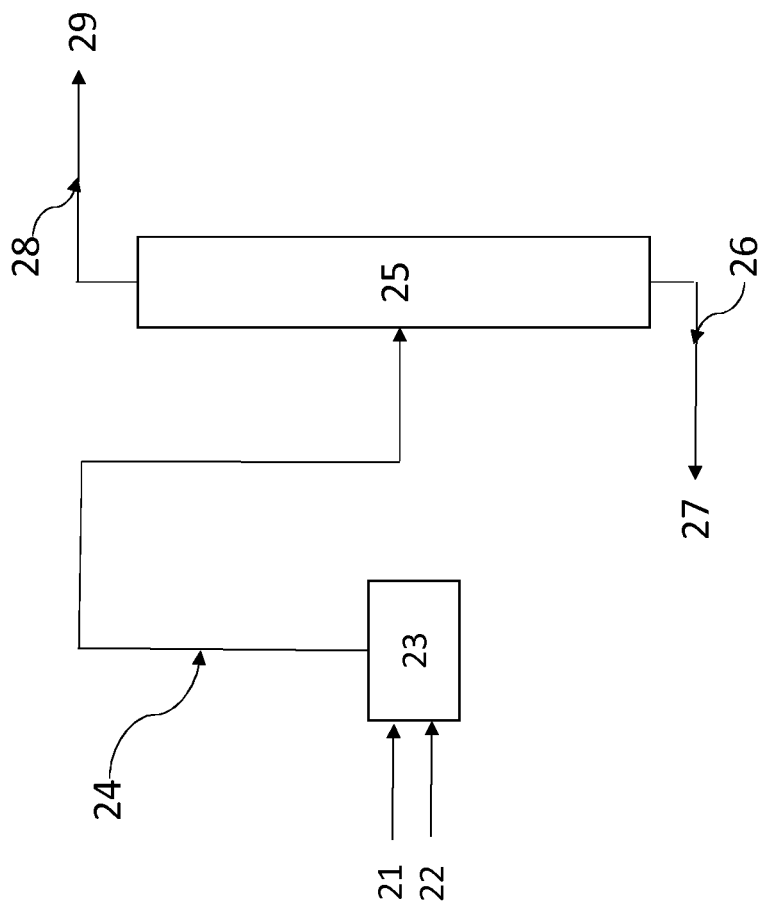
FIG. 2 schematically represents a device for performing a process for producing 2-3,3,3-tetrafluoro-1-propene according to a particular embodiment of the present invention.

FIG. 2 schematically illustrates a device for performing a process for producing 2,3,3,3-tetrafluoropropene according to a particular embodiment of the present invention. Hydrofluoric acid 21 is placed in contact with 1,1,1,2,3-pentachloropropane (240db) 22 in a reactor 23. The mixture obtained and especially comprising 2,3,3,3-tetrafluoro-1-propene, chloromethane (40) and trans-1,3,3,3-tetrafluoro-1-propene (1234ze-E) is recovered at the reactor outlet and conveyed to a distillation column 25 via pipe 24. The mixture may also comprise HCl, HF and heavy impurities or impurities with a boiling point below that of 2,3,3,3-tetrafluoro-1-propene. The stream obtained at the bottom of the distillation column comprising HF and optionally heavy impurities is conveyed to the purification device 27 via pipe 26 to purify HF which will optionally be recycled in 23. The other constituents of the mixture are conveyed via pipe 28 to a purification device 29 for purifying 2,3,3,3-tetrafluoro-1-propene. The purification device 29 may be any of the devices illustrated in FIGS. 1*a*-1*b*.

The catalyst used in the present process for producing 2,3,3,3-tetrafluoropropene may be based, for example, on a metal comprising a transition metal oxide or a derivative or a halide or an oxyhalide of such a metal. Mention may be made, for example, of $FeCl_3$, chromium oxyfluoride, chromium oxides (optionally subjected to fluorination treatments) and chromium fluorides, and mixtures thereof. Other possible catalysts are catalysts supported on carbon, antimony-based catalysts, and aluminum-based catalysts (for example $AlF_3$ and $Al_2O_3$, aluminum oxyfluoride and aluminum fluoride).

Use may be made in general of a chromium oxyfluoride, an aluminum fluoride or oxyfluoride, or an optionally supported catalyst containing a metal such as Cr, Ni, Fe, Zn, Ti, V, Zr, Mo, Ge, Sn, Pb, Mg or Sb.

Reference may be made in this respect to WO 2007/079431 (on page 7, lines 1-5 and 28-32) and EP 939071 (paragraph [0022]), WO 2008/054781 (on page 9, line 22 to page 10, line 34) and WO 2008/040969 (claim 1), to which reference is expressly made.

The catalyst is more particularly preferably chromium-based and it is more particularly a mixed catalyst comprising chromium.

According to one embodiment, a mixed catalyst comprising chromium and nickel is used. The Cr/Ni mole ratio (on the basis of the metal element) is generally from 0.5 to 5, for example from 0.7 to 2, for example about 1. The catalyst may contain from 0.5% to 20% by weight of nickel.

The metal may be present in metallic form or in the form of a derivative, for example an oxide, halide or oxyhalide. These derivatives are preferably obtained by activation of the catalytic metal.

The support is preferably constituted with aluminum, for example alumina, activated alumina or aluminum derivatives, such as aluminum halides and aluminum oxyhalides, for example described in U.S. Pat. No. 4,902,838, or obtained via the activation process described above.

The catalyst may comprise chromium and nickel in an activated or unactivated form, on a support which has optionally been subjected to activation.

Reference may be made to WO 2009/118628 (especially on page 4, line 30 to page 7, line 16), to which reference is expressly made herein.

Another preferred embodiment is based on a mixed catalyst containing chromium and at least one element chosen from Mg and Zn. The atomic ratio of Mg or Zn/Cr is preferably from 0.01 to 5.

Before its use, the catalyst is preferably subjected to activation with air, oxygen or chlorine and/or with HF.

The catalyst is preferably subjected to activation with air or oxygen and HF at a temperature from 100 to 500° C., preferably from 250 to 500° C. and more particularly from 300 to 400° C. The activation time is preferably from 1 to 200 hours and more particularly from 1 to 50 hours.

This activation may be followed by a final fluorination activation step in the presence of an oxidizing agent, HF and organic compounds.

The HF/organic compounds mole ratio is preferably from 2 to 40 and the oxidizing agent/organic compounds mole ratio is preferably from 0.04 to 25. The temperature of the final activation is preferably from 300 to 400° C. and its duration is preferably from 6 to 100 hours.

The gas-phase fluorination reaction may be performed:
  with an HF/compound of formula (I) and/or (II) mole ratio from 3:1 to 150:1, preferably from 4:1 to 125:1 and more particularly preferably from 5:1 to 100:1;
  with a contact time from 3 to 100 seconds, preferably 4 to 75 seconds and more particularly 5 to 50 seconds (volume of catalyst divided by the total entering stream, adjusted to the operating temperature and pressure);
  at a pressure ranging from atmospheric pressure to 20 bar, preferably from 2 to 18 bar and more particularly from 3 to 15 bar;

at a temperature (temperature of the catalytic bed) from 200 to 450° C., preferably from 250 to 400° C. and more particularly from 280 to 380° C.

The duration of the reaction step is typically from 10 to 8000 hours, preferably from 50 to 5000 hours and more particularly preferably from 70 to 1000 hours.

An oxidizing agent, preferably oxygen, may optionally be added during the fluorination reaction. The oxygen/organic compounds mole ratio may be from 0.005 to 2, preferably from 0.01 to 1.5. Oxygen may be introduced in pure form or in the form of air or an oxygen/nitrogen mixture. Oxygen may also be replaced with chlorine.

Method for Selecting the Organic Extracting Agent

The selection of the organic extracting agent is determined by using the Cosmo-RS model implemented in the COSMOTHERM software. For this selected binary couple, a separation factor is calculated for each of the solvents studied via the following equation:

$S_{1,2} = (\gamma_{1,S} * P1)/(\gamma_{2,S} * P2)$ in which $\gamma_{1,S}$ represents the activity coefficient of the first compound 1 in the organic extracting agent under consideration at infinite dilution, P1 represents the saturating vapor pressure of the first compound 1, $\gamma2,S$ represents the activity coefficient of the second compound 2 of the binary couple in the organic extracting agent under consideration at infinite dilution, P2 represents the saturating vapor pressure of the second compound.

An absorption capacity is also calculated for each of the solvents studied and for a binary couple (1,2) under consideration. The absorption capacity is calculated via the formula $C_{2,S} = 1/(\gamma_{2,S})$ in which $\gamma_{2,S}$ represents the activity coefficient of the second compound of the binary couple under consideration in said organic extracting agent studied at infinite dilution.

The calculations are repeated for each organic extracting agent studied. Minimum separation factor and absorption capacity values are identified so as to allow a sufficient separation between the first compound and the second compound of the binary couple (1,2) under consideration. The saturating vapor pressure is considered for a temperature of 25° C.

EXAMPLES

Example 1

To purify 2,3,3,3-tetrafluoro-1-propene, the binary couple 2,3,3,3-tetrafluoro-1-propene/chloromethane (40) and the binary couple 2,3,3,3-tetrafluoro-1-propene/trans-1,3,3,3-tetrafluoro-1-propene (1234ze-E) are considered to select the organic extracting agent. On the basis of the information obtained by the Cosmo-RS model, the solvents given in table 1 below were tested for the extractive distillation of a mixture comprising 2,3,3,3-tetrafluoro-1-propene, chloromethane (40) and trans-1,3,3,3-tetrafluoro-1-propene (1234ze-E).

TABLE 1

Absorption capacity $C_{2,S}$ and separation factor $S_{1,2}$ of the organic extracting agent

| Organic extracting agent | $C_{2,S}$- (40) | $S_{1,2}$ (1234yf/40) | $C_{2,S}$- (1234ze-E) | $S_{1,2}$ (1234yf/ 1234ze-E) |
|---|---|---|---|---|
| Methyl formate | 1.01 | 2.34 | 0.83 | 2.21 |
| Isopropyl acetate | 1.33 | 1.74 | 1.42 | 2.15 |
| 2-Methoxyethanamine | 1.30 | 1.80 | 1.98 | 3.19 |
| tert-Butyl acetate | 1.33 | 1.77 | 1.37 | 2.10 |
| Dioxane | 1.29 | 2.29 | 1.09 | 2.24 |
| 1,3-Dioxane | 1.40 | 2.47 | 1.09 | 2.23 |
| sec-Butyl acetate | 1.34 | 1.69 | 1.45 | 2.12 |
| 1,2-Diaminoethane | 0.97 | 2.88 | 1.29 | 4.43 |
| 1-Methoxy-2-propanol | 0.98 | 2.30 | 0.86 | 2.31 |
| 1,2-Propanediamine | 1.18 | 2.40 | 1.50 | 3.54 |
| n-Butyl acetate | 1.35 | 1.85 | 1.35 | 2.14 |
| 2-Methoxy-1-propanol | 0.99 | 2.29 | 0.87 | 2.31 |
| 1-Ethoxy-2-propanol | 1.15 | 2.01 | 1.12 | 2.27 |
| Hexanal | 1.31 | 2.06 | 1.09 | 1.98 |

The extractive distillations performed with the organic extracting agents collated in table 1 above resulted in separation between, on the one hand, 2,3,3,3-tetrafluoro-1-propene and, on the other hand, chloromethane (40), trans-1,3,3,3-tetrafluoro-1-propene (1234ze-E) and the organic extracting agent. After separation, chloromethane (40) and trans-1,3,3,3-tetrafluoro-1-propene (1234ze-E) remain in solution in the organic extracting agent. The latter was recovered by distillation and thus separated from the chloromethane (40) and the trans-1,3,3,3-tetrafluoro-1-propene (1234ze-E).

The invention claimed is:

1. A process for purifying 2,3,3,3-tetrafluoro-1-propene (1234yf) using a first composition comprising 2,3,3,3-tetrafluoro-1-propene and chloromethane, said process comprising:
    a) placing said first composition in contact with at least one organic extracting agent to form a second composition;
    b) distilling said second composition using extractive distillation to form:
        i) a third composition comprising said at least one organic extracting agent and chloromethane; and
        ii) a stream comprising 2,3,3,3-tetrafluoro-1-propene (1234yf);
    c) recovering and separating said third composition to form a stream comprising said at least one organic extracting agent and a stream comprising chloromethane, wherein said first composition, said second composition and said third composition also comprise trans-1,3,3,3-tetrafluoro-1-propene (1234ze-E); and wherein step c) comprises recovering and separating said third composition, to form a stream comprising said at least one organic extracting agent and a stream comprising chloromethane and trans-1,3,3,3-tetrafluoro-1-propene (1234ze-E).

2. The process as claimed in claim 1, wherein said at least one organic extracting agent comprises a solvent selected from the group consisting of hydrocarbons, halohydrocarbons, alcohol, ketone, amine, ester, ether, aldehyde, nitrile, carbonate, thioalkyl, amide and heterocycle; or the organic extracting agent is difluorodiethylsilane or triethyifluorosilane.

3. The process as claimed in claim 1, wherein the organic extracting agent has a boiling point of between 10 and 150° C.

4. The process as claimed in claim 1, wherein said organic extracting agent has a separation factor $S_{1,2}$ of greater than or equal to 1.1, said separation factor being calculated by the formula $S_{1,2}=(\gamma_{1,S}*P1)/(\gamma_{2,S}*P2)$ wherein
- $\gamma_{1,S}$ represents the activity coefficient of 2,3,3,3-tetrafluoro-1-propene in said organic extracting agent at infinite dilution;
- P1 represents the saturating vapor pressure of 2,3,3,3-tetrafluoro-1-propene;
- $\gamma_{2,S}$ represents the activity coefficient of chloromethane in said organic extracting agent at infinite dilution; and
- P2 represents the saturating vapor pressure of chloromethane.

5. The process as claimed in claim 1, wherein said at least one organic extracting agent has an absorption capacity $C_{2,S}$ of greater than or equal to 0.20, said absorption capacity being calculated by the formula $C_{2,S}=1/(\gamma_{2,S})$ in which $\gamma_{2,S}$ represents the activity coefficient of chloromethane.

6. The process as claimed in claim 1, wherein said at least one organic extracting agent has a separation factor $S_{1,2}$ of greater than or equal to 1.1, said separation factor being calculated by the formula $S_{1,2}=(\gamma_{1,S}*P1)/(\gamma_{2,S}*P2)$ wherein
- $\gamma_{1,S}$ represents the activity coefficient of 2,3,3,3-tetrafluoro-1-propene in said at least one organic extracting agent at infinite dilution;
- P1 represents the saturating vapor pressure of 2,3,3,3-tetrafluoro-1-propene;
- $\gamma_{2,S}$ represents the activity coefficient of trans-1,3,3,3-tetrafluoro-1-propene (1234ze-E) in said at least one organic extracting agent at infinite dilution; and
- P2 represents the saturating vapor pressure of trans-1,3,3,3-tetrafluoro-1-propene (1234ze-E).

7. The process as claimed in claim 1, wherein the first composition is an azeotropic or quasi-azeotropic composition comprising 2,3,3,3,-tetrafluoro-1-propene, chloromethane and trans-1,3,3,3-tetrafluoro-1-propene (1234ze-E).

8. The process as claimed in claim 1, wherein said at least one organic extracting agent is selected from the group consisting of methyl formate, 2-methoxy-1-propene, ethoxyethene, propanone, methyl acetate, isobutanal, isopropyl formate, ethyl acetate, butanone, n-propyl formate, 1,2-dimethoxyethane, isopropyl acetate, 1-methoxy-2-propanamine, 2-methoxyethanamine, 2-methylbutanal, tert-butyl acetate, ethyl propionate, dioxane, 3-pentanone, 2-pentanone, 2-methoxy-1-propanamine, trimethoxymethane, 1,3-dioxane, 3,3-dimethyl-2-butanone, 2-ethoxyethanamine, sec-butyl acetate, n-methyl-1,2-ethanediamine, 4-methyl-2-pentanone, 1,2-diaminoethane, butyronitrile, 1-methoxy-2-propanol, 1,2-propanediamine, 2,6-dimethyl-5-heptenal, 1-(dimethylamino)-2-propanol, diethyl carbonate, n-butyl acetate, 2-hexanone, n-ethylethylenediamine, 5-hexen-2-one, 2-methylpyridine, 2-methoxy-1-propanol, 1-ethoxy-2-propanol, hexanal, 2-(dimethylamino)ethanol, 2-methylpyrazine, 2-ethoxy-1-propanol, 1,3-propanediamine, valeronitrile, 2,6-dimethylpyridine, 4-methyl-2-hexanone, 1-methoxy-2-acetoxypropane, 4-methylpyridine, 2,6-dimethylmorpholine, methyl hexanoate, 2-propoxyethanol and 1-propoxy-2-propanol.

9. The process as claimed in claim 1, further comprising, prior to step a), the following steps:
- i') using a composition comprising 2,3,3,3-tetrafluoro-1-propene, impurities with a boiling point below the boiling point of 2,3,3,3-tetrafluoro-1-propene, chloromethane and optionally heavy impurities and/or trans-1,3,3,3-tetrafluoro-1-propene (1234ze-E);
- ii') distilling said composition from step i') to remove, at the top of the column, impurities with a boiling point below the boiling point of 2,3,3,3-tetrafluoro-1-propene and to form a first stream comprising 2,3,3,3-tetrafluoro-1-propene, chloromethane and optionally heavy impurities and/or trans-1,3,3,3-tetrafluoro-1-propene (1234ze-E), recovered at the bottom of the distillation column;
- iii') optionally, distilling said first stream recovered at the bottom of the distillation column in step ii') to recover, at the top of the column, a second stream comprising 2,3,3,3-tetrafluoro-1-propene, chloromethane (40) and optionally trans-1,3,3,3-tetrafluoro-1-propene (1234ze-E); and, at the bottom of the distillation column, a stream comprising the heavy impurities; wherein said first stream recovered in step ii') or said second stream recovered in step iii') corresponds to said first composition used in step a).

10. A composition comprising 2,3,3,3-tetrafluoropropene, an organic extracting agent, chloromethane and trans-1,3,3,3-tetrafluoro-1-propene (1234ze-E); wherein said organic extracting agent is selected from the group consisting of methyl formate, 2-methoxy-1-propene, ethoxyethene, propanone, methyl acetate, isobutanal, isopropyl formate, ethyl acetate, butanone, n-propyl formate, 1,2-dimethoxyethane, isopropyl acetate, 1-methoxy-2-propanamine, 2-methoxyethanamine, 2-methylbutanal, tert-butyl acetate, ethyl propionate, dioxane, 3-pentanone, 2-pentanone, 2-methoxy-1-propanamine, trimethoxymethane, 1,3-dioxane, 3,3-dimethyl-2-butanone, 2-ethoxyethanamine, sec-butyl acetate, n-methyl-1,2-ethanediamine, 4-methyl-2-pentanone, 1,2-diaminoethane, butyronitrile, 1-methoxy-2-propanol, 1,2-propanediamine, 2,6-dimethyl-5-heptenal, 1-(dimethylamino)-2-propanol, diethyl carbonate, n-butyl acetate, 2-hexanone, n-ethylethylenediamine, 5-hexen-2-one, 2-methylpyridine, 2-methoxy-1-propanol, 1-ethoxy-2-propanol, hexanal, 2-(dimethylamino)ethanol, 2-methylpyrazine, 2-ethoxy-1-propanol, 1,3-propanediamine, valeronitrile, 2,6-dimethylpyridine, 4-methyl-2-hexanone, 1-methoxy-2-acetoxypropane, 4-methylpyridine, 2,6-dimethylmorpholine, methyl hexanoate, 2-propoxyethanol and 1-propoxy-2-propanol.

11. The composition as claimed in claim 10, wherein the organic extracting agent is selected from the group consisting of methyl formate, ethoxyethene, propanone, methyl acetate, isobutanal, isopropyl formate, ethyl acetate, butanone, isopropyl acetate, 2-methoxyethanamine, tert-butyl acetate, dioxane, 3-pentanone, 2-pentanone, 1,3-dioxane, 3,3-dimethyl-2-butanone, sec-butyl acetate, 4-methyl-2-pentanone, 1,2-diaminoethane, 1-methoxy-2-propanol, 1,2-propanediamine, diethyl carbonate, n-butyl acetate, 2-methoxy-1-propanol, 1-ethoxy-2-propanol and hexanal.

12. A composition comprising 2,3,3,3-tetrafluoropropene, an organic extracting agent, chloromethane and trans-1,3,3,3-tetrafluoro-1-propene (1234ze-E); said organic extracting agent having a separation factor $S_{1,2}$ of greater than 1.6, said separation factor being calculated by the formula $S_{1,2}=(\gamma_{1,S}*P1)/(\gamma_{2,S}*P2)$ in which $\gamma_{1,S}$ represents the activity coefficient of 2,3,3,3-tetrafluoropropene in said organic extracting agent at infinite dilution, P1 represents the saturating vapor pressure of 2,3,3,3-tetrafluoropropene, $\gamma_{2,S}$ represents the activity coefficient of chloromethane in said organic extracting agent at infinite dilution, and P2 represents the saturating vapor pressure of chloromethane, wherein the composition comprises between 75% and 99.9% by weight of 2,3,3,3-tetrafluoro-1-propene, between 0.01% and 25% by weight of trans-1,3,3,3-tetrafluoro-1-propene (1234ze-E)

and less than 1% by weight of chloromethane relative to the total weight of the composition.

* * * * *